United States Patent
Tanaka et al.

(10) Patent No.: US 10,194,092 B2
(45) Date of Patent: Jan. 29, 2019

(54) PHOTOGRAPHING APPARATUS AND METHOD CAPABLE OF SETTING APPROPRIATE EXPOSURE TIME PERIODS IN CONSIDERATION OF TEMPORAL CHANGE IN LIGHT

(71) Applicant: FUJIFILM Corporation, Minato-ku, Tokyo (JP)

(72) Inventors: Yasutake Tanaka, Ashigarakami-gun (JP); Yasunori Ohta, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 427 days.

(21) Appl. No.: 14/823,152

(22) Filed: Aug. 11, 2015

(65) Prior Publication Data

US 2016/0057329 A1  Feb. 25, 2016

(30) Foreign Application Priority Data

Aug. 21, 2014 (JP) .................... 2014-168137
Aug. 21, 2014 (JP) .................... 2014-168138

(51) Int. Cl.
*H04N 5/228* (2006.01)
*H04N 5/235* (2006.01)
(Continued)

(52) U.S. Cl.
CPC ........... *H04N 5/2353* (2013.01); *H04N 5/217* (2013.01); *H04N 5/2252* (2013.01);
(Continued)

(58) Field of Classification Search
CPC ............... H04N 5/2356; H04N 5/2353; H04N 5/235–5/243; G03B 7/00–7/28; G03B 9/58–9/62; G03B 2207/00–2207/005
See application file for complete search history.

(56) References Cited

U.S. PATENT DOCUMENTS 6,791,618 B1   9/2004   Shimizu
2009/0161929 A1   6/2009   Oba et al.
(Continued)

FOREIGN PATENT DOCUMENTS

JP   2000-180361 A   6/2000
JP   2004-128546 A   4/2004
(Continued)

OTHER PUBLICATIONS

Japanese Notification of Reasons for Refusal, dated dated Nov. 22, 2016, for Japanese Application 2014-168137, as well as an English translation.
(Continued)

*Primary Examiner* — Sinh Tran
*Assistant Examiner* — Selam T Gebriel
(74) *Attorney, Agent, or Firm* — Birch, Stewart, Kolasch & Birch, LLP

(57) ABSTRACT

There are provided a photographing apparatus and a method capable of photographing a subject a plurality of times sequentially and calculating exposure time periods in consideration of temporal change in light from the subject of the photography. The photographing apparatus includes: a photographing section; a photographic subject light information acquisition section; an exposure time calculation section and an image processing section that adds images sequentially captured through the shots of the photography. Assuming that n is an integer equal to or greater than 2, the exposure time calculation section calculates an exposure time period of an n-th shot on the basis of images captured through an (n−1)th shot or previous shots than the (n−1)th shot of the photography. The photographing section takes each shot of the photography, on the basis of each exposure time period which is calculated by the exposure time calculation section for each shot of the photography.

2 Claims, 12 Drawing Sheets

(51) Int. Cl.
*H04N 5/217* (2011.01)
*H04N 5/225* (2006.01)
*H04N 5/335* (2011.01)
*G01N 21/64* (2006.01)
*G01N 21/76* (2006.01)

(52) U.S. Cl.
CPC ......... *H04N 5/2351* (2013.01); *H04N 5/335* (2013.01); *G01N 21/6456* (2013.01); *G01N 21/76* (2013.01)

(56) References Cited

U.S. PATENT DOCUMENTS

| | | | |
|---|---|---|---|
| 2011/0279706 A1* | 11/2011 | Lesiak | H04N 5/2355 348/229.1 |
| 2013/0070110 A1* | 3/2013 | Yamaguchi | H04N 5/2354 348/207.1 |

FOREIGN PATENT DOCUMENTS

| | | |
|---|---|---|
| JP | 2006-41796 A | 2/2006 |
| JP | 2006-345317 A | 12/2006 |
| JP | 2008-42746 A | 2/2008 |
| JP | 2008-82922 A | 4/2008 |
| JP | 2009-109402 A | 5/2009 |
| JP | 2009-150829 A | 7/2009 |
| JP | 2009-236846 A | 10/2009 |
| JP | 2011-114441 A | 6/2011 |
| JP | 2013-68725 A | 4/2013 |
| JP | 2014-50525 A | 3/2014 |

OTHER PUBLICATIONS

Japanese Notification of Reasons for Refusal, dated dated Nov. 22, 2016, for Japanese Application 2014-168138, as well as an English translation.

Extended European Search Report for European Application No. 15179728.9, dated Jan. 25, 2016.

\* cited by examiner

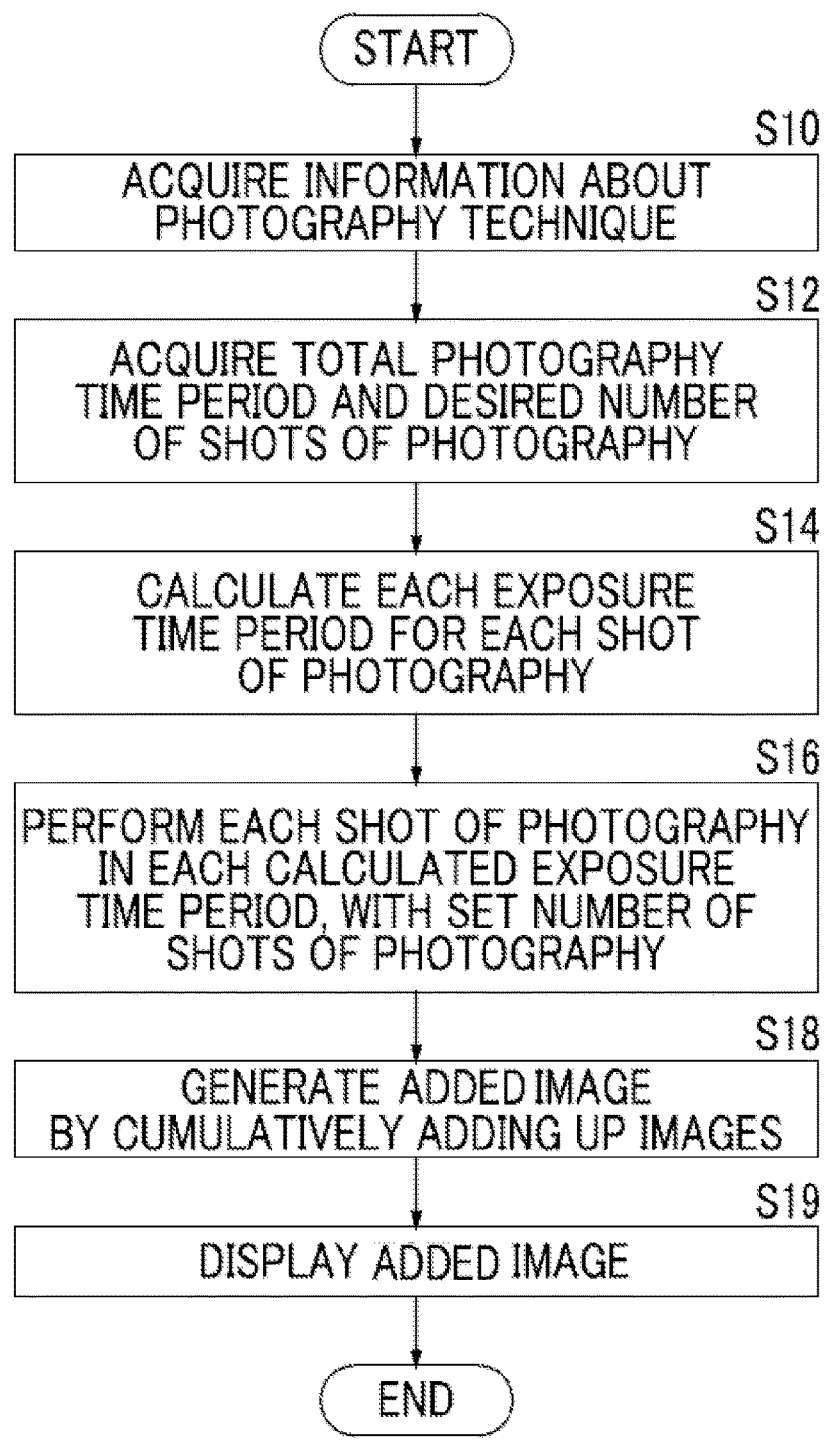

PHOTOGRAPHING APPARATUS AND METHOD CAPABLE OF SETTING APPROPRIATE EXPOSURE TIME PERIODS IN CONSIDERATION OF TEMPORAL CHANGE IN LIGHT

CROSS-REFERENCE TO RELATED APPLICATIONS

The present application claims priority under 35 U.S.C. § 119 to Japanese Patent Application No. 2014-168137, filed on Aug. 21, 2014 and Japanese Patent Application No. 2014-168138, filed on Aug. 21, 2014. Each of the above application(s) is hereby expressly incorporated by reference, in its entirety, into the present application.

BACKGROUND OF THE INVENTION

1. Field of the Invention

The present invention relates to a photographing apparatus and a method capable of photographing a subject, which is placed in a casing, a plurality of times sequentially.

2. Description of the Related Art

In the past, photographing systems, in which a subject is placed in a casing and which photograph a subject by irradiating the subject with light through a light source provided in the casing, have been utilized in various fields. In such photographing systems, a photography technique is selectively used mainly in accordance with a type of a subject. For example, JP2004-128546A, JP2014-050525, JP2009-236846A, and JP2008-042746A disclose photographing systems that generate images by causing an imaging element to capture chemiluminescent, fluorescent or reflected light, which originates from a subject, or transmitted light which is transmitted through the subject.

In a proposal of JP2004-128546A, since an intensity of chemiluminescent light or fluorescent light emitted from a subject is weak, when such light is intended to be photographed, photography is performed a plurality of times sequentially, thereby generating an added image in which images captured through a plurality of shots of the photography are cumulatively added up.

In a proposal of JP2013-68725A, a plurality of shots of pre-photography are taken, light emitting characteristics of a sample are calculated on the basis of a result of the pre-photography, and appropriate exposure time periods of shots of the photography are calculated on the basis of the light emitting characteristics.

SUMMARY OF THE INVENTION

Here, as described above, when photography is performed a plurality of times sequentially, each exposure time period for each shot of the photography may be inappropriately set depending on a user's experience. In this case, if the exposure time period is too short, an image signal with a sufficient magnitude may not be obtained. If the exposure time period is too long, photography efficiency may be lowered.

In the case where chemiluminescent light is photographed, a luminescence intensity of the light has time-varying characteristics in which the intensity is reduced with the passage of time due to an effect of fading of a reagent. In contrast, in the case where fluorescent light is photographed, there is almost no effect of the fading of the reagent, and the luminescence intensity has time-varying characteristics in which the intensity is kept substantially constant.

As described above, the case of capturing chemiluminescent light is different from the case of capturing fluorescent light in temporal change in light from the photographic subject. Therefore, when photography is performed a plurality of times sequentially, if exposure time periods of shots of the photography are set to be the same for respective shots of the light, an appropriate image may not be acquired.

JP2004-128546A, JP2014-050525, and JP2009-236846A do not disclose a method of determining exposure time periods of shots of photography in consideration of the above-mentioned time-varying characteristics of chemiluminescent light and fluorescent light. Further, JP2011-114441A, JP2006-345317A, and JP2006-41796A disclose exposure control which is performed when photography is continuously performed using a camera. However, such documents also do not disclose a method of determining exposure time periods of shots of photography in consideration of the time-varying characteristics of chemiluminescent light and fluorescent light.

JP2013-68725A proposes a method of calculating exposure time periods in consideration of light emitting characteristics of a sample. However, there is no proposal for a method of calculating an exposure time period for each shot of photography which is performed a plurality of times sequentially as described above.

JP2008-042746A proposes a method of synthesizing images which are acquired through a plurality of shots of photography, and a method of performing photography by changing the exposure time period. However, there is no proposal for a method of calculating an exposure time period for each shot of photography in consideration of the above-mentioned time-varying characteristics of chemiluminescent light.

In consideration of the above problems, the present invention has an object to provide a photographing apparatus and a photographing method capable of setting appropriate exposure time periods in consideration of temporal change in light caused by fading of a reagent and the like.

According to a first aspect of the present invention, there is provided a photographing apparatus including: a photographing section that photographs a subject a plurality of times sequentially; a photographic subject light information acquisition section that acquires information about light from the subject of the photography; and an exposure time calculation section that selects a method of calculating an exposure time period of the photography according to time-varying characteristics of the light on the basis of the information about the light acquired by the photographic subject light information acquisition section, and that calculates each exposure time period for each shot of the photography, by using the selected method of calculating the exposure time period, in which the photographing section performs the photography, on the basis of each exposure time period which is calculated by the exposure time calculation section for each shot of the photography.

The photographing apparatus according to the first aspect of the present invention may further include an image processing section that adds images sequentially captured through the shots of the photography; and a display control section that displays an added image in which the images are added by the image processing section.

In the case where the light from the subject of the photography is chemiluminescent light, the exposure time calculation section may integrate a function indicating time-varying characteristics of the chemiluminescent light, and thereby calculate each exposure time period, at which an integral value of the function is the same in each shot of the photography, for each shot of the photography.

As the function, an exponential function may be used.

In the case where the light from the subject of the photography is fluorescent light, the exposure time calculation section may make the respective exposure time periods of the respective shots of the photography the same.

The photographing apparatus according to the first aspect of the present invention may further include a reagent information acquisition section that acquires information about a reagent used at the time of photographing the subject. The exposure time calculation section may select a method of calculating the exposure time period of the photography on the basis of the information about the light and the information about the reagent, and calculate each exposure time period for each shot of the photography by using the selected method of calculating the exposure time period.

The exposure time calculation section may have a table in which the method of calculating the exposure time period of the photography is associated with the information about the light and the information about the reagent.

The photographing section may perform pre-photography before the photography is sequentially performed. The exposure time calculation section may determine each exposure time period for each shot of the photography on the basis of an image which is acquired by the pre-photography.

The exposure time calculation section may calculate each exposure time period, at which a signal increment of each image at each shot of the photography or a sum value of the signal increments of each image at each shot of the photography is equal to a preset target signal amount, for each shot of the photography.

The display control section may display a total photography time period which is obtained by adding up all the exposure time periods of the photography.

According to a second aspect of the present invention, there is provided a method of photographing a subject a plurality of times sequentially, the method including: acquiring information about light from the subject of the photography; selecting a method of calculating an exposure time period of the photography according to time-varying characteristics of the light on the basis of the information about the light acquired, and calculating each exposure time period for each shot of the photography, by using the selected method of calculating the exposure time period; and performing the photography, on the basis of each exposure time period which is calculated for each shot of the photography.

According to a third aspect of the present invention, there is provided a photographing apparatus including: a photographing section that photographs a subject a plurality of times sequentially; an exposure time calculation section that calculates each exposure time period for each shot of the photography; and an image processing section that adds images sequentially captured through the shots of the photography, in which when n is an integer equal to or greater than 2, the exposure time calculation section calculates an exposure time period of an n-th shot on the basis of image captured through an (n−1)th shot or previous shots than the (n−1)th shot of the photography, and in which the photographing section takes each shot of the photography, on the basis of each exposure time period which is calculated by the exposure time calculation section for each shot of the photography.

In the photographing apparatus according to the third aspect of the present invention, the exposure time calculation section may calculate the exposure time period of the n-th shot of the photography, on the basis of images captured through the (n−1)th shot or previous shots than the (n−1)th shot of the photography performed a plurality of times.

The photographing section may perform pre-photography before a first shot of the photography. The exposure time calculation section may calculate the exposure time period of the n-th shot of the photography, on the basis of an image of a single shot or images of a plurality of shots of the pre-photography and an image of a single shot or images of the (n−1)th shot or previous shots than the (n−1)th shot of the photography performed a plurality of times.

The exposure time calculation section may calculate an exposure time period of the first shot of the photography on the basis of the images of the plurality of shots of the pre-photography.

The photographing apparatus according to the third aspect of the present invention may further include a photographic subject light information acquisition section that acquires information about light from the subject of the photography. The exposure time calculation section may select a method of calculating an exposure time period of each shot of the photography according to time-varying characteristics of the light on the basis of the information about the light from the subject of the photography, the information being acquired by the photographic subject light information acquisition section, and may calculate each exposure time period for each shot of the photography, by using the selected method of calculating the exposure time period.

The photographing apparatus according to the third aspect of the present invention may further include a reagent information acquisition section that acquires information about a reagent used at the time of photographing the subject. The exposure time calculation section may select a method of calculating the exposure time period of each shot of the photography on the basis of the information about the light of the subject of the photography and the information about the reagent, and may calculate each exposure time period of each shot of the photography by using the selected method of calculating the exposure time period.

The exposure time calculation section may set a part of the image as a pixel for attention or a region for attention, and may calculate the exposure time period on the basis of a signal value of the pixel for attention or the region for attention.

The photographing apparatus according to the third aspect of the present invention may further include a region for attention designation receiving section that receives designation of the pixel for attention or the region for attention.

In the case where the signal value of the pixel for attention or the region for attention is saturated, the image processing section may add an image, which is multiplied by a time proportionality factor, to an image before the saturation.

In the case where the signal value of the pixel for attention or the region for attention is saturated, the exposure time calculation section may set an auxiliary pixel for attention or an auxiliary region for attention at a position different from that of the pixel for attention or the region for attention, and calculate the exposure time period on the basis of the signal value of the auxiliary pixel for attention or the auxiliary region for attention.

In the case where the signal value of the auxiliary pixel for attention or the auxiliary region for attention is saturated, the image processing section may add an image, which is multiplied by a time proportionality factor, to an image before the saturation.

The photographing apparatus according to the third aspect of the present invention may further include a display control section that displays an added image in which the images are added up by the image processing section.

The display control section may display a total exposure time period which is obtained by adding up all the exposure time periods of the photography.

According to a fourth aspect of the present invention, there is provided a method of photographing a subject a plurality of times sequentially, the method including: calculating an exposure time period of an n-th shot on the basis of images captured through an (n−1)th shot or previous shots than the (n−1)th shot of the photography, assuming that n is an integer equal to or greater than 2; taking each shot of the photography, on the basis of each exposure time period which is calculated for each shot of the photography; and adding up respective images captured through the respective shots of the photography.

In the photographing apparatus and method according to the first and second aspects of the present invention, when a subject is photographed a plurality of times sequentially, the information about the light from the photographic subject is acquired, the method of calculating the exposure time period of the photography according to time-varying characteristics of the light is selected on the basis of the information about the light acquired, and each exposure time period for each shot of the photography is calculated by using the selected method of calculating the exposure time period, that is, the method of calculating the exposure time period of the photography is switched in accordance with time-varying characteristics of light from the photographic subject such as chemiluminescent light or fluorescent light. Therefore, it is possible to automatically calculate an appropriate exposure time period in consideration of temporal change in light caused by fading of the reagent and the like, regardless of a user's experience.

In the photographing apparatus and method according to the third and fourth aspects of the present invention, when a subject is photographed a plurality of times sequentially, the exposure time period of the n-th shot of the photography is calculated on the basis of the images captured through the (n−1)th shot or previous shots than the (n−1)th shot of the photography, that is, the exposure time period is calculated on the basis of the images which are acquired until the previous shot of the photography. Therefore, it is possible to automatically calculate an appropriate exposure time period in consideration of temporal change in light at a time point of the previous shot of the photography, regardless of a user's experience.

BRIEF DESCRIPTION OF THE DRAWINGS

FIG. 5 is a flowchart illustrating operations of a photographing system using a photographing apparatus according to a first embodiment of the present invention.

DESCRIPTION OF THE PREFERRED EMBODIMENTS

Figure 1:
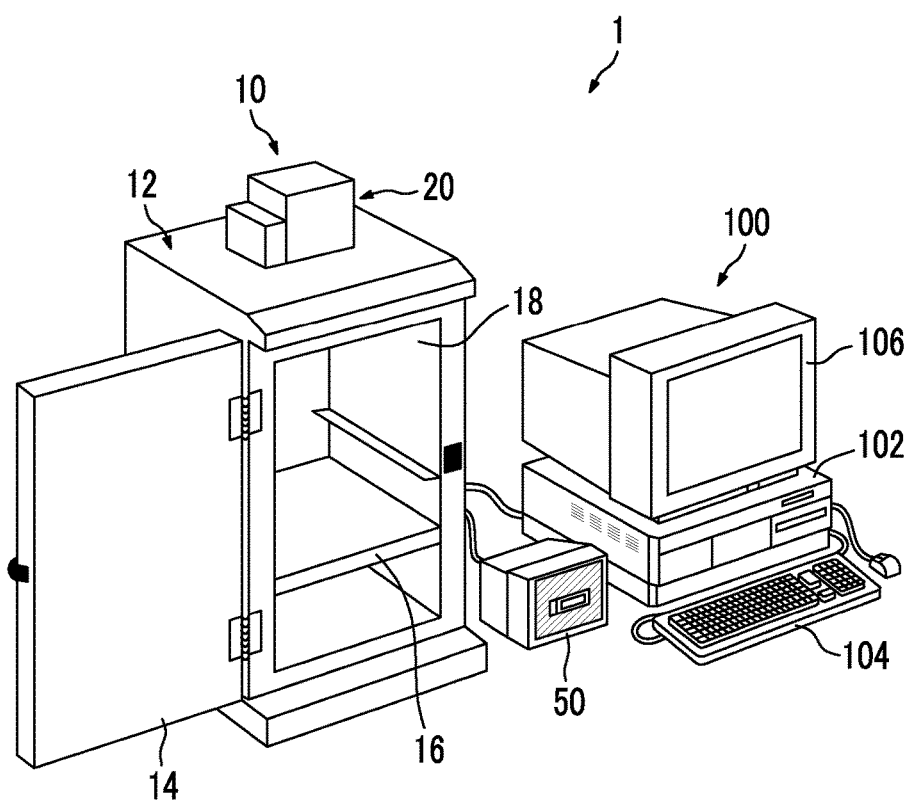
FIG. 1 is a schematic perspective view of a photographing system using a photographing apparatus according to an embodiment of the present invention.
Figure 2:
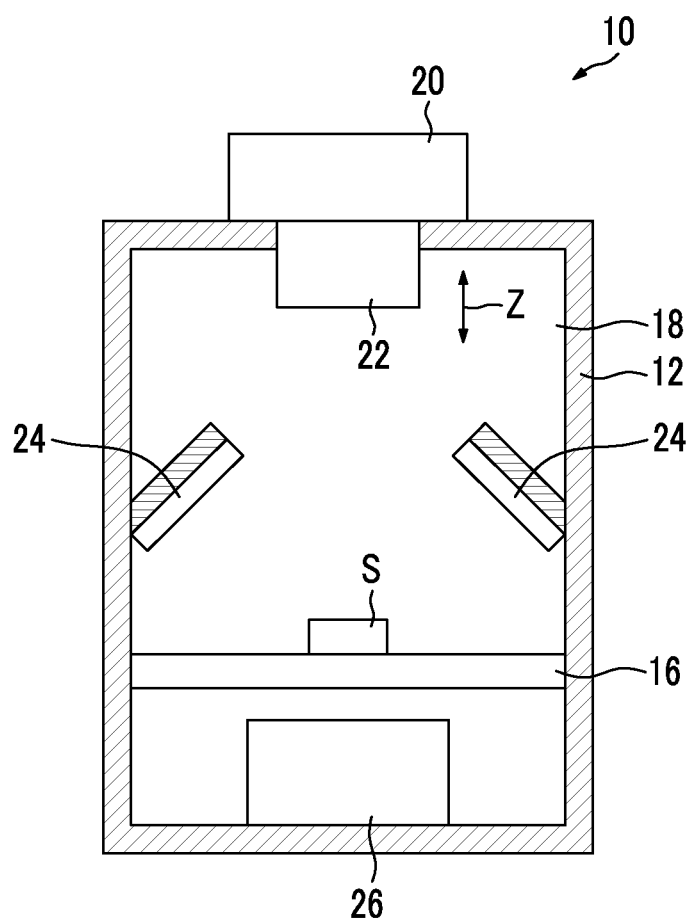
FIG. 2 is a schematic sectional view illustrating an internal configuration of the photographing apparatus according to the embodiment of the present invention.
Figure 3:
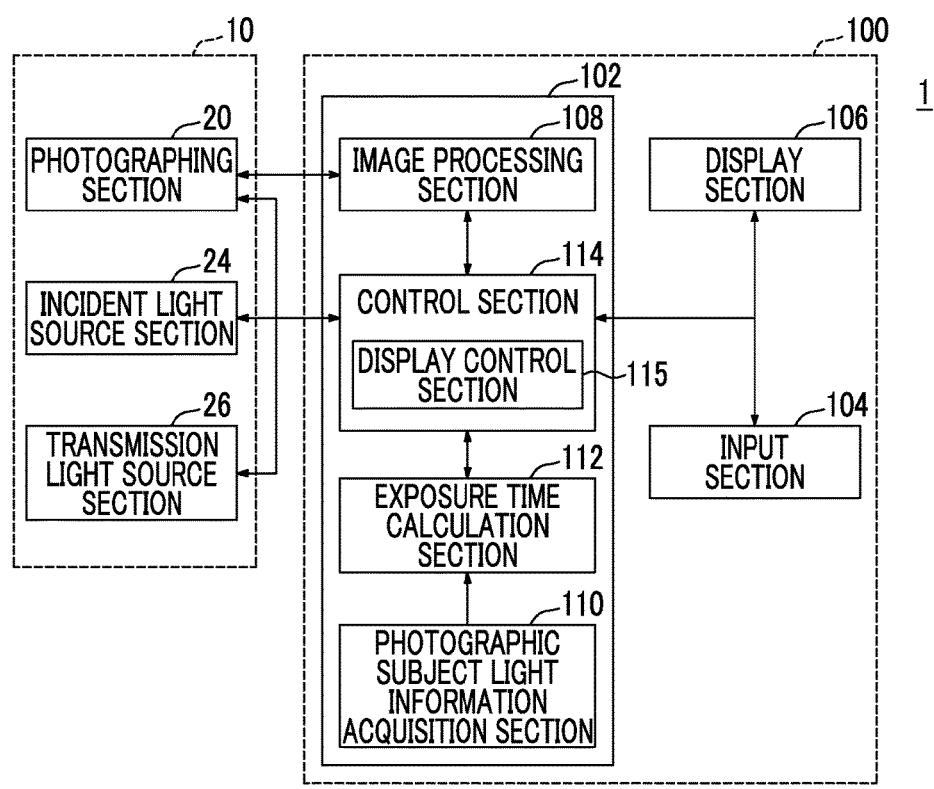
FIG. 3 is a schematic block diagram of the photographing apparatus according to the embodiment of the present invention.

Hereinafter, a photographing system 1 using a photographing apparatus and a photographing method according to a first embodiment of the present invention will be described in detail with reference to drawings. FIG. 1 is a schematic perspective view illustrating a photographing system of the present embodiment. FIG. 2 is a schematic sectional view illustrating an internal configuration of a photographing apparatus of the present embodiment. FIG. 3 is a schematic block diagram illustrating the photographing system of the present embodiment.

As shown in FIGS. 1 and 2, a photographing system 1 of the present embodiment includes a dark box 10 and a photography control device 100.

The dark box 10 includes: a casing 12 that has a door 14; a stage 16 on which a subject S is provided; a photographing section 20; a lens section 22; an incident light source section 24; a transmission light source section 26; and a subject observation monitor 50.

The casing 12 has a hollow portion 18 which is a substantially rectangular parallelepiped, and the stage 16, on which the subject S is placed, is provided in the casing 12. Further, in the casing 12, the door 14 shown in FIG. 1 is mounted to be capable of opening and closing. Thus, a user opens the door 14, places the subject S on the stage 16, and thereafter closes the door 14, whereby the subject S can be housed in the casing 12. The casing 12 constitutes a dark box by which outside light does not enter into the hollow portion 18. The stage 16 is formed of a material which transmits light originating from the transmission light source section 26.

The photographing section 20 is fixed onto an upper surface of the casing 12, and includes an imaging element such as a cooled charge coupled device (CCD) image sensor or a complementary metal oxide semiconductor (CMOS) image sensor, thereby detecting light reflected from the subject S, light emitting from the subject S, or light transmitted through the subject S, and generating an image signal. The image signal generated by the photographing section 20 is subjected to for example amplification processing, and is thereafter output to the photography control device 100.

The lens section 22 is mounted on the photographing section 20. The lens section 22 includes, for example, a plurality of lenses, and the lenses are provided to be movable in a direction of an arrow Z in order to bring the subject S into focus. Further, the lens section 22 also includes, for example, optical elements such as a diaphragm and an excitation light cut filter, thereby adjusting a wavelength or a light amount of the detected light.

Each of the incident light source section 24 and the transmission light source section 26 has, for example, an excitation light source and a white light source for fluorescent photography, and is configured such that the light source is switched as necessary under control of the photography control device 100. For example, in the case where photography for detecting fluorescent light emitted from a fluorescently-labeled subject S is performed, the subject S is irradiated with excitation light originating from the incident light source section 24 or the transmission light source section 26. In the case where photography for detecting light reflected from the subject S is performed, the subject S is irradiated with white light originating from the incident light source section 24. In the case where photography for detecting light transmitted through the subject S is performed, the subject S is irradiated with white light originating from the transmission light source section 26.

The subject observation monitor 50 displays a state on the stage 16 which is photographed by a small camera (not shown) provided on the upper side of the casing 12. Thereby, by checking a height of the stage 16 or a position of the subject S placed on the stage 16, the height of the stage or the position of the subject can be adjusted such that the subject S is placed appropriately for the photography.

The photography control device 100 is formed of, for example, a personal computer, and includes a control device main body 102, an input section 104, and a display section 106. The photography control device 100 controls operations of the photographing section 20, the incident light source section 24, and the transmission light source section 26 belonging to the dark box 10. That is, the dark box 10 is controlled by the photography control device 100, thereby photographing the subject S. In the present embodiment, the photographing apparatus according to the embodiment of the present invention includes the photographing section 20 in the dark box 10, and a photographic subject light information acquisition section 110 and an exposure time calculation section 112 of the photography control device 100.

Here, the photographing system 1 of the present embodiment captures chemiluminescent light or fluorescent light emitted from the subject S, but the intensity of such light is weak. Accordingly, in the case where chemiluminescent light or fluorescent light is intended to be photographed, the photographing system 1 of the present embodiment performs photography a plurality of times sequentially, thereby generating an added image in which the images captured through a plurality of shots of the photography are cumulatively added up. Consequently, in the case where chemiluminescent light or fluorescent light is intended to be photographed, the photography control device 100 of the present embodiment controls the photographing section 20 of the dark box 10 such that it performs photography a plurality of times sequentially as described above.

A control device main body 102 includes, as shown in FIG. 3, an image processing section 108, the photographic subject light information acquisition section 110, the exposure time calculation section 112, and a control section 114.

The image processing section 108 receives an input of image signals which are output from the photographing section 20, and performs signal processing (such as noise removal processing or sharpness processing) on the image signals. Further, in the case where chemiluminescent light or fluorescent light emitted from a subject is intended to be photographed, the image processing section 108 of the present embodiment generates added image data by cumulatively adding up image signals of the images which are sequentially photographed by the photographing section 20. It should be noted that cumulatively adding up the image signals of the images means that, for example, assuming that an image signal of a first shot of the photography is G1, an image signal of a second shot of the photography is G2, and an image signal of a third shot of the photography is G3, the added image is calculated by G1+G2, or the added image is calculated by G1+G2+G3.

The photographic subject light information acquisition section 110 acquires information about a technique of photographing the subject S as the information about the light from the photographic subject. The information about the technique of photographing the subject S is input by a user through the input section 104. As the photography technique, there are chemiluminescent photography and fluorescent photography, and the photography technique will be described in detail later.

The exposure time calculation section 112 selects a method of calculating each exposure time period for each shot of the photography in the above-mentioned case of performing photography a plurality of times sequentially on the basis of the information about the photography technique acquired by the photographic subject light information acquisition section 110, and calculates each exposure time period for each shot of the photography by using the selected method of calculating the exposure time period. The exposure time calculation section 112 will be described later in detail.

The control section 114 includes, for example, a central processing unit (CPU), a read only memory (ROM), and the like. The control section 114 integrally controls operations of the respective sections in the dark box 10 and the photography control device 100. Further, the control section 114 includes a display control section 115, and the display control section 115 displays the above-mentioned added image and the like on the display section 106.

The display section 106 is formed of a display apparatus such as a cathode ray tube (CRT) display or a liquid crystal display, and displays the added image which is generated by the image processing section 108 as described above. Further, the display section 106 displays a setting screen for giving an instruction or performing various kinds of setting on the respective sections of the dark box 10.

The input section 104 includes a mouse, a keyboard, and the like. A user gives an instruction or performs various kinds of setting on the respective sections of the dark box 10 by using the input section 104. The user sets and inputs the information about the photography technique and information about a reagent name and the like by using the input section 104. The set and input information is stored in, for example, a storage section (not shown) which is provided in the control section 114.

Since the photographing system 1 of the present embodiment has the above-mentioned configuration, it is possible to perform photography using four photography techniques in accordance with a purpose of the photography or a type of a subject. The four photography techniques include: a photography technique (hereinafter referred to as a first photography technique) of detecting chemiluminescent light emitted from a subject; a photography technique (hereinafter referred to as a second photography technique) of detecting fluorescent light emitted from a subject; a photography technique (hereinafter referred to as a third photography technique) of detecting reflected light which is reflected from a subject; and a photography technique (hereinafter referred to as a fourth photography technique) of detecting transmitted light which is transmitted through a subject. It should be noted that the photography technique of the present embodiment is determined in accordance with a type of light from the photographic subject such as chemiluminescent light, fluorescent light, reflected light, transmitted light, or the like.

In the first photography technique, when subject molecules excited by chemical reaction return to a ground state, a phenomenon (chemiluminescence), in which energy is emitted as light, is used. Thereby, it is possible to perform, for example, genetic analysis, research and tests on biological tissue for disorders and aging, evaluation of deterioration in organic compounds and polymer compounds, and the like. For example, a labeling substance, which causes chemiluminescence when the substance comes into contact with a chemiluminescence substrate, may label a photographic subject substance in a subject, and may thereafter generate chemiluminescent light by bringing the chemiluminescence substrate into contact with the labeling substance. It should be noted that, in the first photography technique, irradiation of light emitted from the incident light source section 24 and the transmission light source section 26 is not performed.

In the second photography technique, excitation light is emitted from the incident light source section 24 or the transmission light source section 26, and fluorescent light, which is emitted from the fluorescent substance labeling the photographic subject substance in a subject, is detected. As the subject of the second photography technique, for example, there is a gel support including deoxyribonucleic acid (DNA) fragments which are fluorescently labeled and separated by electrophoresis. Using this photographing system 1, distribution of DNA fragments in the gel support can be visualized as an image, and can be evaluated.

In the third photography technique, for example, white light is emitted as illumination light from the incident light source section 24, and reflected light, which is reflected from a subject under the illumination light, is detected. Thereby, it is possible to obtain a digital image by photoelectrically reading a reflective original such as a photo. Further, in the fourth photography technique, for example, white light is emitted as illumination light from the transmission light source section 26, and transmitted light, which is transmitted through a subject under the illumination light, is detected. Thereby, it is possible to obtain a digital image by photoelectrically reading a transparent original such as a film.

Here, in the photographing system 1 of the present embodiment, in the case where chemiluminescent light is photographed in a manner as the above-mentioned first photography technique, or in the case where fluorescent light is photographed in a manner as the second photography technique, the subject S is photographed a plurality of times sequentially. At this time, each exposure time period, which is set through a user's experience, for each shot of the photography may be an inappropriate exposure time period. Specifically, if the exposure time period is too short, an image signal with a sufficient magnitude may not be obtained, and if the exposure time period is too long, this may cause deterioration in photography efficiency.

In the case where chemiluminescent light is photographed by the above-mentioned first photography technique, the luminescence intensity of the light has time-varying characteristics in which the intensity is reduced with the passage of time due to the effect of fading of the reagent. In contrast, in the case where fluorescent light is photographed by the above-mentioned second photography technique, there is almost no effect of the fading of the reagent.

Figure 4A:
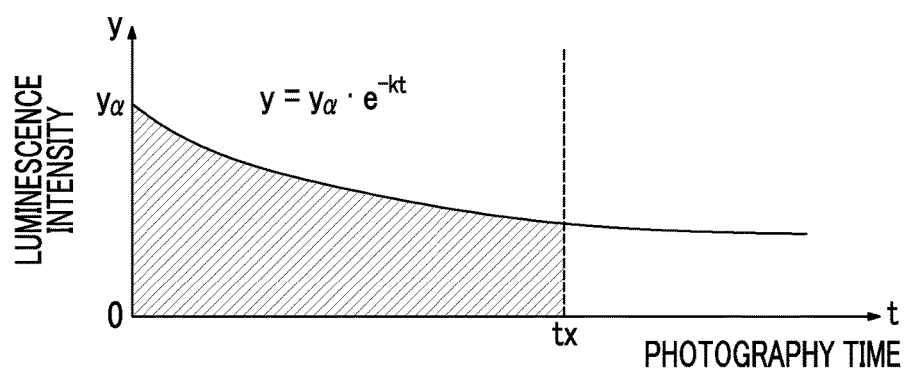
FIG. 4A is a graph illustrating time-varying characteristics of a luminescence intensity of chemiluminescent light.
Figure 4B:
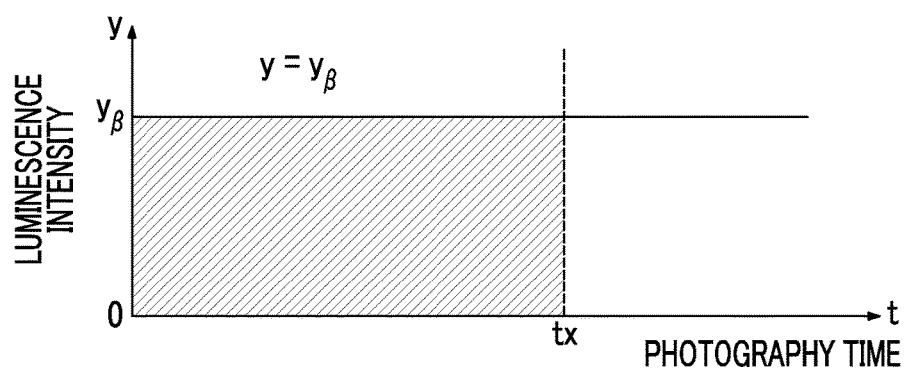
FIG. 4B is a graph illustrating time-varying characteristics of a luminescence intensity of fluorescent light.

FIG. 4A is a graph illustrating time-varying characteristics of the luminescence intensity of chemiluminescent light, and FIG. 4B is a graph illustrating time-varying characteristics of the luminescence intensity of fluorescent light. As shown in FIG. 4A, in most cases, the luminescence intensity of the chemiluminescent light may be attenuated exponentially, that is, attenuated depending on $y=y_\alpha \cdot \exp(-k \cdot t)$ ($y_\alpha$ and $k$ are positive constants). The reason for this is that, as concentrations of reactants in an excited state are reduced in accordance with advancement of chemical reaction, the intensity of the chemiluminescent light is reduced. $y_\alpha$ and $k$ are determined by the substance which causes chemiluminescence.

In contrast, as shown in FIG. 4B, there is almost no attenuation of the luminescence intensity of the fluorescent light, and the luminescence intensity of the fluorescent light is maintained at a constant value of ideally $y=y_\beta$ ($y_\beta$ is a positive constant) as long as excitation light is supplied. The reason for this is that the fluorescent light is generated without destruction of the fluorescent substance. $y_\beta$ is determined by the fluorescent substance. The fluorescent light may be attenuated in accordance with the type of the substance. Even in this case, an attenuation rate of the luminescence intensity according to the passage of time is smaller than that in the case of chemiluminescent light. Consequently, in this case, the time-varying characteristics of the fluorescent light may be approximated by a linear function $y=-a \cdot t+y_\gamma$ ($a$ and $y_\gamma$ are positive constants).

As described above, the first photography technique is different from the second photography technique in temporal change in light from the photographic subject. Therefore, when photography is performed a plurality of times sequentially, if exposure time periods of shots of the photography are set to be the same for respective photography techniques, an appropriate image may not be acquired.

In the case where the added image is generated by cumulatively adding up the images acquired through the plurality shots of the photography as the photographing system 1 of the present embodiment, as the number of images subjected to the addition increases, noise included in each image also increases. Therefore, image quality deteriorates. Consequently, it is preferable that the number of images subjected to the addition is as small as possible, and it is preferable that the number of images is set such that an intensity of the image signal of the added image is sufficient.

Accordingly, in the photographing system 1 of the present embodiment, the exposure time calculation section 112 calculates exposure time periods by switching the method of calculating the exposure time period for each shot of the photography in accordance with the photography technique. The exposure time periods are exposure time periods in which the above-mentioned temporal change in light caused by fading of the reagent is considered and which end at a desired number of shots of the photography.

Specifically, in the exposure time calculation section 112 of the present embodiment, an attenuation function of approximating the time-varying characteristics of the chemiluminescent light shown in FIG. 4A is set in advance, and thus the exposure time calculation section 112 calculates each exposure time period for each shot of the photography on the basis of the attenuation function. For example, in the case where the photography technique is the first photography technique, the exposure time calculation section 112 reads and integrates the attenuation function of approximating the time-varying characteristics of the chemiluminescent light shown in FIG. 4A, thereby calculating each exposure time period for each shot of the photography such that values of integrals of the function at the shots of the photography are the same. It should be noted that the attenuation function is not limited to a decreasing exponential function, and may be a linear function of which a slope is negative. Further, the value of the integral described herein is defined as a value which is obtained by setting a length of a predetermined photography interval in the function shown in FIG. 4A as the exposure time period and integrating the attenuation function with respect to the length of the exposure time period.

On the other hand, in the case where the photography technique is the second photography technique, the effect of fading of the reagent is infinitesimal. Hence, the exposure time calculation section 112 makes the exposure time periods for the shots of the photography the same. Specifically, a value, which is obtained by dividing a desired total photography time period by a desired number of shots of the photography, is calculated as each exposure time period for each shot of the photography.

In addition, in cases of the third and fourth photography techniques, a value of an appropriate exposure time period depends on a reflectance or a transmittance of a stage and an intensity of the illumination light, and thus the value scarcely changes regardless of a subject. Consequently, a preset value can be used as the exposure time period. As a result, also regarding the number of shots of the photography, photography is performed once, without performing photography a plurality of times as the first and second photography techniques.

Next, the operations of the photographing system 1 of the present embodiment will be described with reference to the flowchart shown in FIG. 5. Here, a description will be given focusing on the method of calculating the exposure time period for each shot of the photography when chemiluminescent light and fluorescent light are photographed a plurality of times sequentially.

First, a user sets and inputs the information about the photography technique through the input section 104, and the set and input information about the photography technique is acquired by the photographic subject light information acquisition section 110 (S10).

Next, a user sets and inputs the total photography time period and the desired number of shots of the photography through the input section 104, and the set and input total photography time period and the set and input desired number of shots of the photography are acquired by the exposure time calculation section 112 (S12). The total photography time period is defined as a time period from start of the first shot of the photography to end of the final shot of the photography. The desired number of shots of the photography is defined as the number of shots of the photography at which it is expected that an amount of noise of the added image is restricted to be within a desired range.

Then, the exposure time calculation section 112 selects a method of calculating an exposure time period for each shot of the photography which is performed a plurality of times, on the basis of the information about the photography technique acquired by the photographic subject light information acquisition section 110, and calculates each exposure time period for each shot of the photography on the basis of the selected method of calculating the exposure time period, the total photography time period which is set and input by a user, and the desired number of shots of the photography (S14).

Specifically, in the case where the information about the photography technique is information indicating the first photography technique, the exposure time calculation section 112 reads and integrates the above-mentioned preset attenuation function of approximating the time-varying characteristics of the chemiluminescent light, and calculates each exposure time period for each shot of the photography such that the values of the integrals of the function at respective shots of which the number is set and input by a user are the same.

In contrast, in the case where the information about the photography technique is information indicating the second photography technique, the exposure time calculation section 112 calculates a value, which is obtained by dividing the set and input total photography time period by the set and input number of shots of the photography, as each exposure time period for each shot of the photography. That is, in the case of the second photography technique, since the luminescence intensity of fluorescent light scarcely changes with the passage of time, as described above, the exposure time periods are set to be the same by setting the value, which is obtained by dividing the total photography time period by the number of shots of the photography, as each exposure time period for each shot of the photography. Thereby, signal increments of images of the shots of the photography are substantially the same.

The exposure time period for each shot of the photography, which is calculated by the exposure time calculation section 112, is output to the control section 114. The control section 114 outputs a control signal to the photographing section 20 on the basis of the input exposure time period for each shot of the photography. The photographing section 20 performs photography a plurality of times on the basis of the input control signal, and sequentially outputs signals of the photographed images to the image processing section 108 (S16). The image processing section 108 generates an added image signal by cumulatively adding up the sequentially input image signals, and outputs the added image signal to the display control section 115 (S18).

The display control section 115 generates a display control signal on the basis of the input added image signal, and outputs the display control signal to the display section 106, thereby causing the display section 106 to display the added image (S19). It should be noted that, as the added image displayed on the display section 106, only the added image, in which all the photographed images are added up, may be displayed, and the image of the first shot of the photography and added images, which are generated for shots of the photography, may be also displayed. That is, for example, in the case where photography is performed three times, the following images may be arranged and displayed: the first shot image of the photography; an added image in which the first shot image of the photography and the second shot image of the photography are added up; and an added image in which the first shot image of the photography, the second shot image of the photography, and the third shot image of the photography are added up.

Figure 6:
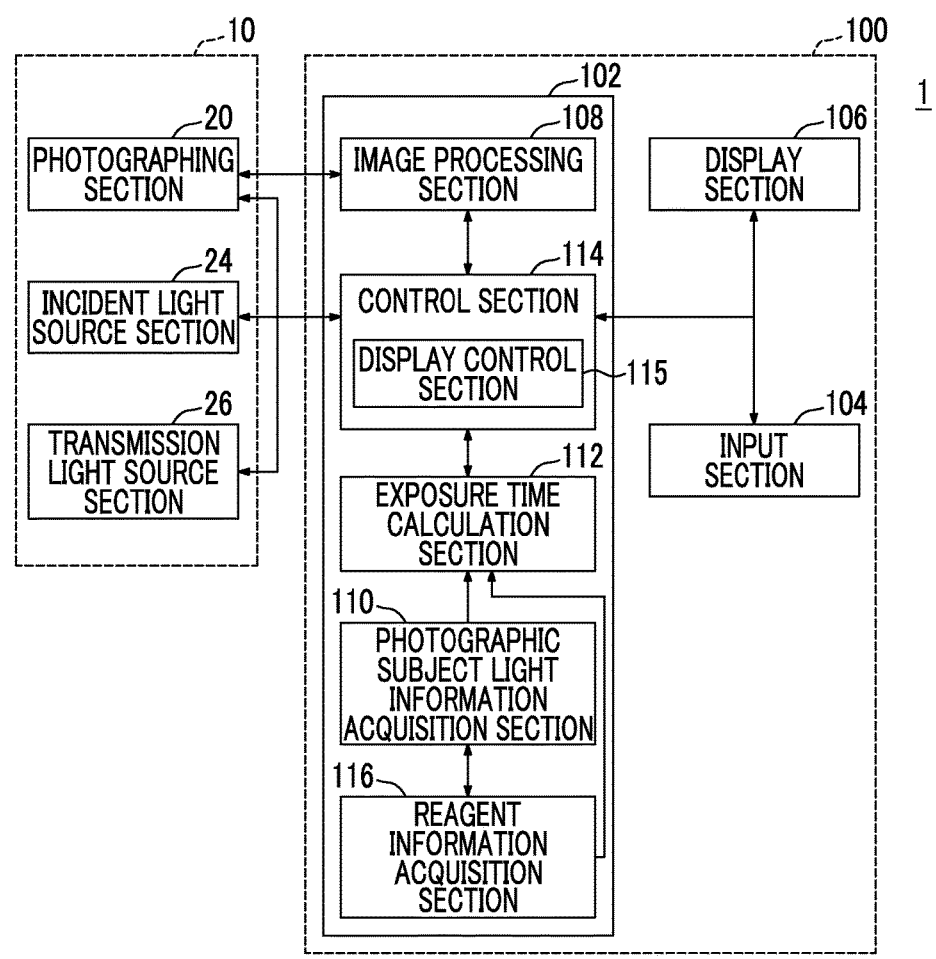
FIG. 6 is a schematic block diagram illustrating a modification example of the photographing apparatus shown in FIG. 3.

In the photographing system 1 of the above-mentioned embodiment, as shown in FIG. 6, a reagent information acquisition section 116 may be further provided, and the exposure time calculation section 112 may select the method of calculating the exposure time period for each shot of the photography on the basis of the information of the reagent acquired by the reagent information acquisition section 116, and may calculate each exposure time period for each shot of the photography by using the selected method of calculating the exposure time period. The information about the reagent is set and input by a user through the input section 104. For example, the information is information about a substance (for example, a chemiluminescence substrate) relating to chemiluminescence in the case where chemiluminescent light is photographed, and is information about a fluorescent substance in the case where fluorescent light is photographed.

Specifically, for example, a table as the following Table 1 may be set in the exposure time calculation section 112 in advance. In the table, pieces of the information about the photography technique and the reagent are associated with functions which are used when calculating the exposure time period for each shot of the photography. The exposure time calculation section 112 may acquire a corresponding function with reference to the table on the basis of the information about the photography technique acquired by the photographic subject light information acquisition section 110 and the information about the reagent acquired by the reagent information acquisition section 116, and may calculate each exposure time period for each shot of the photography by using the function in a manner same way as the above-mentioned manner. It should be noted that, as the functions which are set in the table, a numerical expression indicating the function may be set, and types of the function such as exponential functions, constant functions, and linear functions and coefficients of the functions may be set in the table.

For example, the item No. 1 is a case where there is no setting about the reagent name in the first photography technique. In this case, the exposure time calculation section 112 acquires the attenuation function $F_0$, and calculates each exposure time period for each shot of the photography by using the attenuation function $F_0$. Further, for example, the item No. 5 is a case where the fluorescent substance name $B_1$ is set and input as the reagent name in the second photography technique. In this case, the exposure time calculation section 112 acquires the attenuation function $G_1$, and calculates each exposure time period for each shot of the photography by using the attenuation function $G_1$.

TABLE 1

| No. | Photography technique (detection target) | Reagent Name | Function |
|---|---|---|---|
| 1 | First Photography Technique | — | $F_0: y = y_\alpha \cdot \exp(-kt)$ |
| 2 | (Chemiluminescent Light) | $A_1$ | $F_1: y = y_\alpha \cdot \exp(-k_1 t)$ |
| 3 |  | $A_2$ | $F_2: y = y_\alpha \cdot \exp(-k_2 t)$ |
| 4 | Second Photography Technique | — | $G_0: y = -a \cdot t + y_\gamma$ |

TABLE 1-continued

| No. | Photography technique (detection target) | Reagent Name | Function |
|---|---|---|---|
| 5 | (Fluorescent Light) | $B_1$ | $G_1: y = -a_1 \cdot t + y_\gamma$ |
| 6 |  | $B_2$ | $G_2: y = -a_2 \cdot t + y_\gamma$ |
| 7 |  | $B_3$ | $G_3: y = y_\gamma$ |

It is preferable to set Table 1 such that a user may modify the items thereof and may add another item thereto. For example, it can be considered that exponential approximation may be changed to linear approximation, the slope of linear approximation may be changed, or a new item may be added. If contents of Table 1 can be changed using the input section 104, for example, various kinds of reagent can be handled. Further, in the case where the light amount of the illumination light is changed by deterioration of the light source, approximation can be performed on the time-varying characteristics of the illumination light through the attenuation function or the constant function in which the deterioration of the light source is considered.

In the above-mentioned embodiment, the time-varying characteristics of chemiluminescent light are approximated by the exponential function, but may be approximated by a linear function if fading is negligible.

Next, a photographing system using a photographing apparatus and a photographing method according to a second embodiment of the present invention will be described. The photographing system of the second embodiment is the same as that of the first embodiment in a schematic apparatus configuration, but the method of calculating the exposure time period for each shot of the photography is different from that of the first embodiment. Hereinafter, a description will be given focusing on differences from the first embodiment.

In the photographing system of the first embodiment, a user sets and inputs the desired number of shots of the photography and the total photography time period, whereby each exposure time period for each shot of the photography is calculated on the basis of the desired number, the time period, and the preset attenuation function. The photographing system of the second embodiment performs pre-photography before actual photography, where the exposure time calculation section 112 determines the attenuation function used when calculating each exposure time period for each shot of the photography on the basis of an image acquired through the pre-photography, and calculates each exposure time period for each shot of the photography on the basis of the desired number of shots of the photography and target signal amounts of the shots of the photography which are set and input by a user through the attenuation function.

Figure 7:
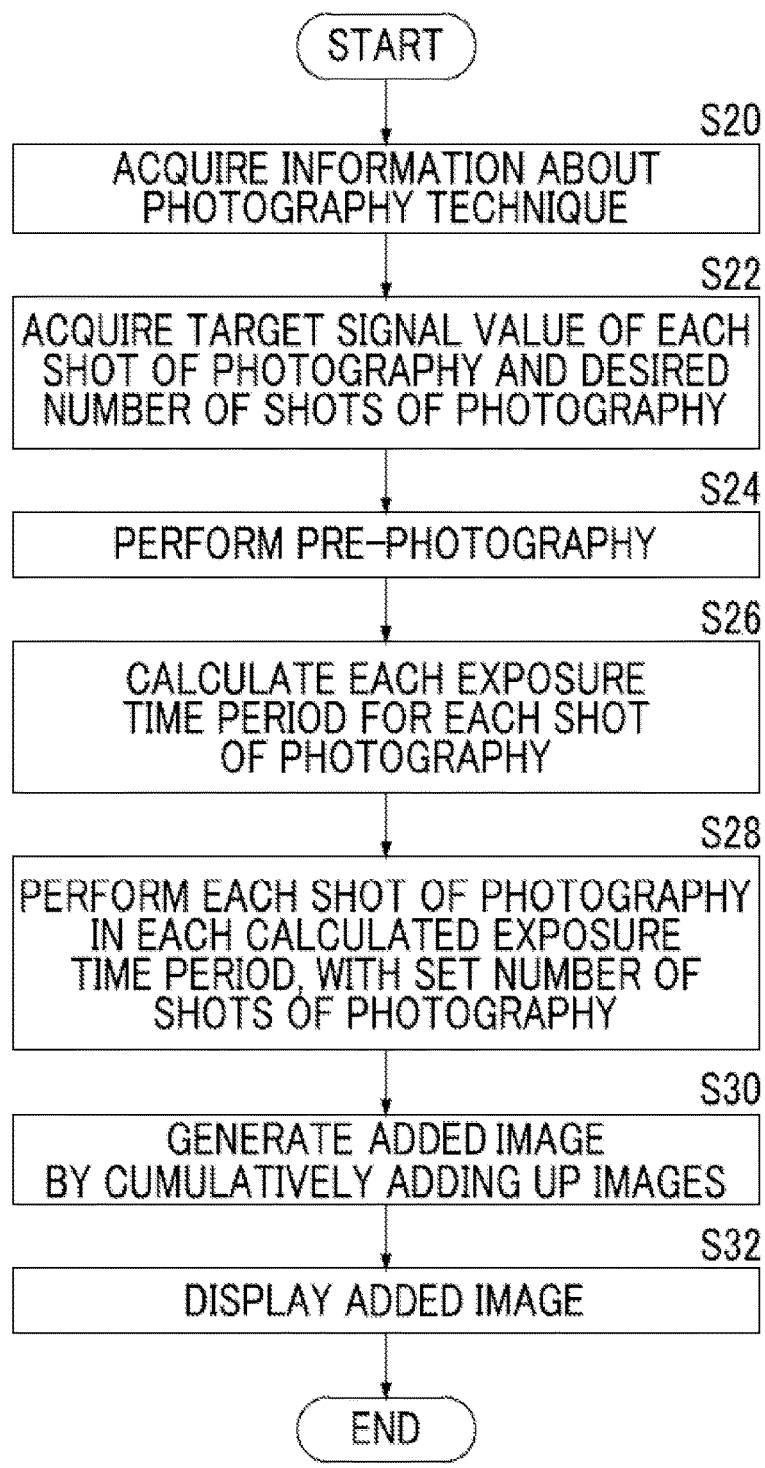
FIG. 7 is a flowchart illustrating operations of a photographing system using a photographing apparatus according to a second embodiment of the present invention.

It should be noted that the actual photography means photography which is performed to obtain an image for analyzing and examining a subject, and the pre-photography means photography which is performed in advance to obtain information for determining an exposure time period of the actual photography. For example, the pre-photography is performed by acquiring an exposure time period of the pre-photography according to a designated photography technique with reference to a table in which the exposure time periods of the pre-photography are associated with the photography techniques and performing photography with this exposure time period. Hereinafter, referring to the flowchart shown in FIG. 7, operations of the photographing system of the second embodiment will be described.

First, a user sets and inputs the information about the photography technique through the input section 104, and the set and input information about the photography technique is acquired by the photographic subject light information acquisition section 110 (S20).

Next, a user sets and inputs the target signal amounts of the image signals of shots of the photography and the desired number of shots of the photography through the input section 104, and the set and input target signal amounts of the image signals of shots of the photography and the set and input desired number of shots of the photography are acquired by the exposure time calculation section 112 (S22). The target signal amount of the image signal of each shot of the photography is a target value of a signal amount which is intended to be acquired in each shot of the photography, and is a value which is arbitrarily set by a user.

Subsequently, the photographing section 20 is controlled on the basis of the control signal which is output from the control section 114 of the photography control device 100, and performs pre-photography (S24). The image signal acquired by the pre-photography is output to the exposure time calculation section 112.

The exposure time calculation section 112 reads a function corresponding to a photography technique on the basis of the information about the photography technique acquired by the photographic subject light information acquisition section 110, determines an initial value of the function on the basis of the image signal acquired by the pre-photography, and calculates each exposure time period for each shot of the photography on the basis of the determined function and the desired number of shots of the photography and the target signal amounts of the shots of the photography which are set and input by a user (S26).

Specifically, in the case where the information about the photography technique is information indicating the first photography technique, the exposure time calculation section 112 reads the above-mentioned preset attenuation function $y=y_\alpha \cdot \exp(-k \cdot t)$ of approximating the time-varying characteristics of the chemiluminescent light. Then, a signal value per the unit time period is acquired by dividing the image signal acquired by the pre-photography by the exposure time period of the pre-photography, and the signal value is set as $y_\alpha$, thereby determining the attenuation function. It should be noted that the coefficient k of the attenuation function is set in advance. Further, as described above, the coefficient k may be set on the basis of the information about the reagent.

As the image signal of the pre-photography used for when the signal value per the unit time period is calculated, it is possible to use a maximum value, a representative value, an average value, or a mode value in the image. Alternatively, a maximum value, a representative value, an average value, or a mode value in a predetermined region of concern in the image acquired by the pre-photography may be used. For example, the region of concern may be designated by a user through the input section 104 while the user views the image of the pre-photography displayed on the display section 106. In addition, an important region in a subject may be automatically detected, and the detected region may be set as the region of concern.

Then, the exposure time calculation section 112 calculates each exposure time period, at which a signal increment obtained through each shot of the photography is equal to the target signal amount which is set and input by a user, by using the attenuation function which is determined as described above.

In contrast, in the case where the information about the photography technique is information indicating the second photography technique, the exposure time calculation section 112 acquires the signal value per the unit time period by dividing the image signal, which is acquired by the pre-photography, by the exposure time period of the pre-photography, and divides the target signal amount, which is set and input by a user, by the signal value per the unit time period for each shot of the photography, thereby calculating each exposure time period for each shot of the photography.

The exposure time period for each shot of the photography, which is calculated by the exposure time calculation section 112, is output to the control section 114. The control section 114 outputs a control signal to the photographing section 20 on the basis of the input exposure time period for each shot of the photography. The photographing section 20 performs photography a plurality of times on the basis of the input control signal, and sequentially outputs signals of the photographed images to the image processing section 108 (S28). The image processing section 108 generates an added image signal by cumulatively adding up the sequentially input image signals, and outputs the added image signal to the display control section 115 (S30).

The display control section 115 generates a display control signal on the basis of the input added image signal, and outputs the display control signal to the display section 106, thereby causing the display section 106 to display the added image (S32).

In the photographing system of the second embodiment, each exposure time period for each shot of the photography is calculated such that the signal increment of each image at each shot of the photography is equal to the preset target signal amount. However, the present invention is not limited to this, and each exposure time period for each shot of the photography may be calculated such that a sum value of the signal increments of each image at each shot of the photography is equal to the preset target signal amount.

In the photographing system of the second embodiment, the total photography time period, which is obtained by adding up the exposure time periods of all the shots of the photography, is calculated, and the display control section 115 causes the display section 106 to display the total photography time period. Further, also in the photographing system of the first embodiment, the display control section 115 causes the display section 106 to display the set and input total photography time period.

In the photographing system of the second embodiment, it is preferable that a sensitivity of the photography is increased by performing binning when pre-photography is performed. When the binning is performed as described above, the signal value per the unit time period of the pre-photography is used, and is converted into an initial signal value $Q_m$ per the unit time period in the actual photography, on the basis of the following Expression 1. In the following Expression 1, $B_p$ is a binning number of the pre-photography, $B_m$ is a binning number of the actual photography, $Q_p$ is the image signal of the pre-photography, and $T_p$ is the exposure time period of the pre-photography.

$$Q_m = \frac{Q_p}{T_p} \frac{B_m}{B_p} \qquad \text{Expression 1}$$

In the photographing system of the second embodiment, a preset value is used as the coefficient k of the attenuation function. However, pre-photography may be performed twice, and the coefficient k may be calculated, using image signals acquired by two shots of the pre-photography, on the basis of the following Expression 2. In the following Expression 2, $Q_{p1}$ is a signal value per the unit time period of the first shot of the pre-photography, $Q_{p2}$ is a signal value per the unit time period of the second shot of the pre-photography, and $T_g$ is a time period from a time point of the first shot of the pre-photography to a time point of the second shot of the pre-photography. By performing pre-photography twice in such a manner, for example, even if a reagent having unclear time-varying characteristics like a new reagent is photographed, it is possible to appropriately set the coefficient k.

$$k = \frac{\ln(Q_{p1}) - \ln(Q_{p2})}{T_g} \qquad \text{Expression 2}$$

Hereinafter, a photographing system 1 using a photographing apparatus and a photographing method according to a third embodiment of the present invention will be described in detail with reference to the drawings. A schematic perspective view of the photographing system of the third embodiment is the same as that of the photographing system of the first embodiment. Further, an internal configuration of the photographing apparatus of the third embodiment is the same as the internal configuration of the photographing apparatus of the first embodiment. Furthermore, a schematic block diagram illustrating the photographing system of the third embodiment is the same as the block diagram of the photographing system of the first embodiment.

The photographing system 1 of the third embodiment includes a dark box 10 and a photography control device 100.

The dark box 10 includes: a casing 12 that has a door 14; a stage 16 on which a subject S is provided; a photographing section 20; a lens section 22; an incident light source section 24; a transmission light source section 26; and a subject observation monitor 50.

The casing 12 has a hollow portion 18 which is a substantially rectangular parallelepiped, and the stage 16, on which the subject S is placed, is provided in the casing 12. Further, in the casing 12, the door 14 is mounted to be capable of opening and closing. Thus, a user opens the door 14, places the subject S on the stage 16, and thereafter closes the door 14, whereby the subject S can be housed in the casing 12. The casing 12 constitutes a dark box by which outside light does not enter into the hollow portion 18. The stage 16 is formed of a material which transmits light originating from the transmission light source section 26.

The photographing section 20 is fixed onto an upper surface of the casing 12, and includes an imaging element such as a cooled charge coupled device (CCD) image sensor or a complementary metal oxide semiconductor (CMOS) image sensor, thereby detecting light reflected from the subject S, light emitting from the subject S, or light transmitted through the subject S, and generating an image signal. The image signal generated by the photographing section 20 is subjected to for example amplification processing, and is thereafter output to the photography control device 100.

The lens section 22 is mounted on the photographing section 20. The lens section 22 includes, for example, a plurality of lenses, and the lenses are provided to be movable in a direction of an arrow Z in order to bring the subject S into focus. Further, the lens section 22 also includes, for example, optical elements such as a diaphragm and an excitation light cut filter, thereby adjusting a wavelength or a light amount of the detected light.

Each of the incident light source section 24 and the transmission light source section 26 has, for example, an excitation light source and a white light source for fluorescent photography, and is configured such that the light source is switched as necessary under control of the photography control device 100. For example, in the case where photography for detecting fluorescent light emitted from the fluorescently-labeled subject S is performed, the subject S is irradiated with excitation light originating from the incident light source section 24 or the transmission light source section 26. In the case where photography for detecting light reflected from the subject S is performed, the subject S is irradiated with white light originating from the incident light source section 24. If photography for detecting light transmitted through the subject S is performed, the subject S is irradiated with white light originating from the transmission light source section 26.

The subject observation monitor 50 displays a state on the stage 16 which is photographed by a small camera (not shown) provided on the upper side of the casing 12. Thereby, by checking a height of the stage 16 or a position of the subject S placed on the stage 16, the height of the stage or the position of the subject can be adjusted such that the subject S is placed appropriately for the photography.

The photography control device 100 is formed of, for example, a personal computer, and includes a control device main body 102, an input section 104, and a display section 106. The photography control device 100 controls operations of the photographing section 20, the incident light source section 24, and the transmission light source section 26 belonging to the dark box 10. That is, the dark box 10 is controlled by the photography control device 100, thereby photographing the subject S. In the third embodiment, the photographing apparatus according to the third embodiment of the present invention includes the photographing section 20 in the dark box 10, and an exposure time calculation section 112 and an image processing section 108 of the photography control device 100.

Here, the photographing system 1 of the third embodiment captures chemiluminescent light or fluorescent light emitted from the subject S, but the intensity of such light is weak. Accordingly, in the case where chemiluminescent light or fluorescent light is intended to be photographed, the photographing system 1 of the third embodiment performs photography a plurality of times sequentially, thereby generating an added image in which the images captured through a plurality of shots of the photography are cumulatively added up. Consequently, in the case where chemiluminescent light or fluorescent light is intended to be photographed, the photography control device 100 of the third embodiment controls the photographing section 20 of the dark box 10 such that it performs photography a plurality of times sequentially as described above.

A control device main body 102 includes, the image processing section 108, a photographic subject light information acquisition section 110, the exposure time calculation section 112, and a control section 114.

The image processing section 108 receives an input of image signals which are output from the photographing section 20, and performs signal processing (such as noise removal processing or sharpness processing) necessary for the image signals. Further, in the case where chemiluminescent light or fluorescent light emitted from a subject is intended to be photographed, the image processing section 108 of the third embodiment generates added image data by cumulatively adding up image signals of the images which are sequentially photographed by the photographing section 20. It should be noted that cumulatively adding up the image signals of the images means that, for example, assuming that an image signal of a first shot of the photography is G1, an image signal of a second shot of the photography is G2, and an image signal of a third shot of the photography is G3, the added image is calculated by G1+G2, or the added image is calculated by G1+G2+G3.

The photographic subject light information acquisition section 110 acquires the information about the light from the photographic subject. The photographic subject light information acquisition section 110 of the third embodiment acquires information which indicates whether the photographic subject is chemiluminescent or fluorescent. Specifically, the photographic subject light information acquisition section 110 of the third embodiment acquires the information as the information about the technique of photographing the subject S. The information about the technique of photographing the subject S is input by a user through the input section 104. It should be noted that the photography technique will be described in detail later.

The exposure time calculation section 112 calculates each exposure time period for each shot of the photography in the case of performing photography a plurality of times sequentially as described above. Specifically, the exposure time calculation section 112 of the third embodiment calculates the exposure time period of the n-th shot of the photography on the basis of the images captured through (n−1)th (n is an integer equal to or greater than 2) shot or previous shots than the (n−1)th shot of the photography. Further, the exposure time calculation section 112 of the third embodiment selects a method of calculating each exposure time period for each shot of the photography on the basis of the information about the photography technique further acquired by the photographic subject light information acquisition section 10, and calculates each exposure time period for each shot of the photography by using the selected method of calculating the exposure time period. A specific method of calculating the exposure time period in the exposure time calculation section 112 will be described in detail later.

The control section 114 includes, for example, a central processing unit (CPU), a read only memory (ROM), and the like. The control section 114 integrally controls operations of the respective sections in the dark box 10 and the photography control device 100. Further, the control section 114 includes a display control section 115, and the display control section 115 displays the above-mentioned added image and the like on the display section 106.

The display section 106 is formed of a display apparatus such as a cathode ray tube (CRT) display or a liquid crystal display, and displays the added image which is generated by the image processing section 108 as described above. Further, the display section 106 displays a setting screen for giving an instruction or performing various kinds of setting on the respective sections of the dark box 10.

The input section 104 includes a mouse, a keyboard, and the like. A user gives an instruction or performs various kinds of setting on the respective sections of the dark box 10 by using the input section 104. The user sets and inputs the information about the photography technique and information about a reagent name and the like by using the input section 104. The set and input information is stored in, for example, a storage section (not shown) which is provided in the control section 114.

Since the photographing system 1 of the third embodiment has the above-mentioned configuration, it is possible to perform photography using four photography techniques in accordance with a purpose of the photography or a type of a subject. The four photography techniques include: the first photography technique, the second photography technique, the third photography technique, and the fourth photography technique described above.

In the first photography technique, when subject molecules excited by chemical reaction return to a ground state, a phenomenon (chemiluminescence), in which energy is emitted as light, is used. Thereby, it is possible to perform, for example, genetic analysis, research and tests on biological tissue for disorders and aging, evaluation of deterioration in organic compounds and polymer compounds, and the like. For example, a labeling substance, which causes chemiluminescence when the substance comes into contact with a chemiluminescence substrate, may label a photographic subject substance in a subject, and may thereafter generate chemiluminescent light by bringing the chemiluminescence substrate into contact with the labeling substance. It should be noted that, in the first photography technique, irradiation of light emitted from the incident light source section 24 and the transmission light source section 26 is not performed.

In the second photography technique, excitation light is emitted from the incident light source section 24 or the transmission light source section 26, and fluorescent light, which is emitted from the fluorescent substance labeling the photographic subject substance in a subject, is detected. As the subject of the second photography technique, for example, there is a gel support including deoxyribonucleic acid (DNA) fragments which are fluorescently labeled and separated by electrophoresis. Using this photographing system 1, distribution of DNA fragments in the gel support can be visualized as an image, and can be evaluated.

In the third photography technique, for example, white light is emitted as illumination light from the incident light source section 24, and reflected light, which is reflected from a subject under the illumination light, is detected. Thereby, it is possible to obtain a digital image by photoelectrically reading a reflective original such as a photo. Further, in the fourth photography technique, for example, white light is emitted as illumination light from the transmission light source section 26, and transmitted light, which is transmitted through a subject under the illumination light, is detected. Thereby, it is possible to obtain a digital image by photoelectrically reading a transparent original such as a film.

Here, in the photographing system 1 of the third embodiment, in the case where chemiluminescent light is photographed in a manner as the above-mentioned first photography technique, or in the case where fluorescent light is photographed in a manner as the second photography technique, the subject S is photographed a plurality of times sequentially. At this time, each exposure time period, which is set through a user's experience, for each shot of the photography may be an inappropriate exposure time period. If the exposure time period is too short, an image signal with a sufficient magnitude may not be obtained, and if the exposure time period is too long, this may cause deterioration in photography efficiency.

In a manner as the above-mentioned first photography technique, if chemiluminescent light is photographed, the luminescence intensity of the light has time-varying characteristics in which the intensity is reduced with the passage of time due to the effect of fading of the reagent. In contrast, in a manner as the above-mentioned second photography technique, in the case where fluorescent light is photographed, there is almost no effect of the fading of the reagent.

FIG. 4A is a graph illustrating time-varying characteristics of the luminescence intensity of chemiluminescent light, and FIG. 4B is a graph illustrating time-varying characteristics of the luminescence intensity of fluorescent light. As shown in FIG. 4A, in most cases, the luminescence intensity of the chemiluminescent light may be attenuated exponentially, that is, attenuated depending on $y=y_\alpha \cdot \exp(-k \cdot t)$ ($y_\alpha$ and k are positive constants). The reason for this is that, as concentrations of reactants in an excited state are reduced in accordance with advancement of chemical reaction, the intensity of the chemiluminescent light is reduced. In addition, $y_\alpha$ and k are determined by the substance which causes chemiluminescence.

In contrast, as shown in FIG. 4B, there is simply almost no attenuation of the luminescence intensity of the fluorescent light, and the luminescence intensity of the fluorescent light is maintained at a constant value of ideally $y=y_\beta$ ($y_\beta$ is a positive constant) as long as excitation light is supplied. The reason for this is that the fluorescent light is generated without destruction of the fluorescent substance. In addition, $y_\beta$ is determined by the fluorescent substance. The fluorescent light may be attenuated in accordance with the type of the substance. Even in this case, an attenuation rate of the luminescence intensity according to the passage of time is smaller than that in the case of chemiluminescent light. Consequently, in this case, the time-varying characteristics of the fluorescent light may be approximated by a linear function $y=-a \cdot t + y_\gamma$ (a and $y_\gamma$ are positive constants).

As described above, the first photography technique is different from the second photography technique in temporal change in light from the photographic subject. Therefore, when photography is performed a plurality of times sequentially, if exposure time periods of shots of the photography are set to be the same for respective photography techniques, an appropriate image may not be acquired.

In the case where the above-mentioned time-varying characteristics of chemiluminescent light or fluorescent light are known in advance, the time-varying characteristics are set in advance, and calculation of the exposure time period may be performed on the basis of the set time-varying characteristics. However, these set time-varying characteristics may be different from the time-varying characteristics of light of the subject S to be actually photographed. In this case, it is difficult to calculate an appropriate exposure time period.

In a manner as the photographing system 1 of the third embodiment, in the case where the added image is generated by cumulatively adding up the images acquired through the plurality shots of the photography, as the number of images subjected to the addition increases, noise included in each image also increases. Therefore, image quality deteriorates. Consequently, it is preferable that the number of images subjected to the addition is as small as possible, and it is preferable that the number of images is set such that an intensity of the image signal of the added image is sufficient.

Therefore, the exposure time calculation section 112 of the third embodiment calculates the appropriate exposure time period according to the time-varying characteristics of the light at the time of actual photography, regardless of a user's experience. Hence, as described above, the exposure time period of the n-th shot of the photography is calculated on the basis of the images captured through (n−1)th (n is an integer equal to or greater than 2) shot or previous shots than the (n−1)th shot of the photography. Further, by switching the calculation method according to the photography technique when calculating each exposure time period for each shot of the photography in such a manner, exposure time periods, in which the above-mentioned temporal change in light caused by fading of the reagent is considered and which end at a desired number of shots of the photography, are calculated.

In addition, in cases of the third and fourth photography techniques, a value of an appropriate exposure time period depends on a reflectance or a transmittance of a stage and an intensity of the illumination light, and thus the value scarcely changes regardless of a subject. Consequently, a preset value can be used as the exposure time period. As a result, also regarding the number of shots of the photography, photography is performed once, without performing photography a plurality of times in a manner as the first and second photography techniques.

Figure 8:
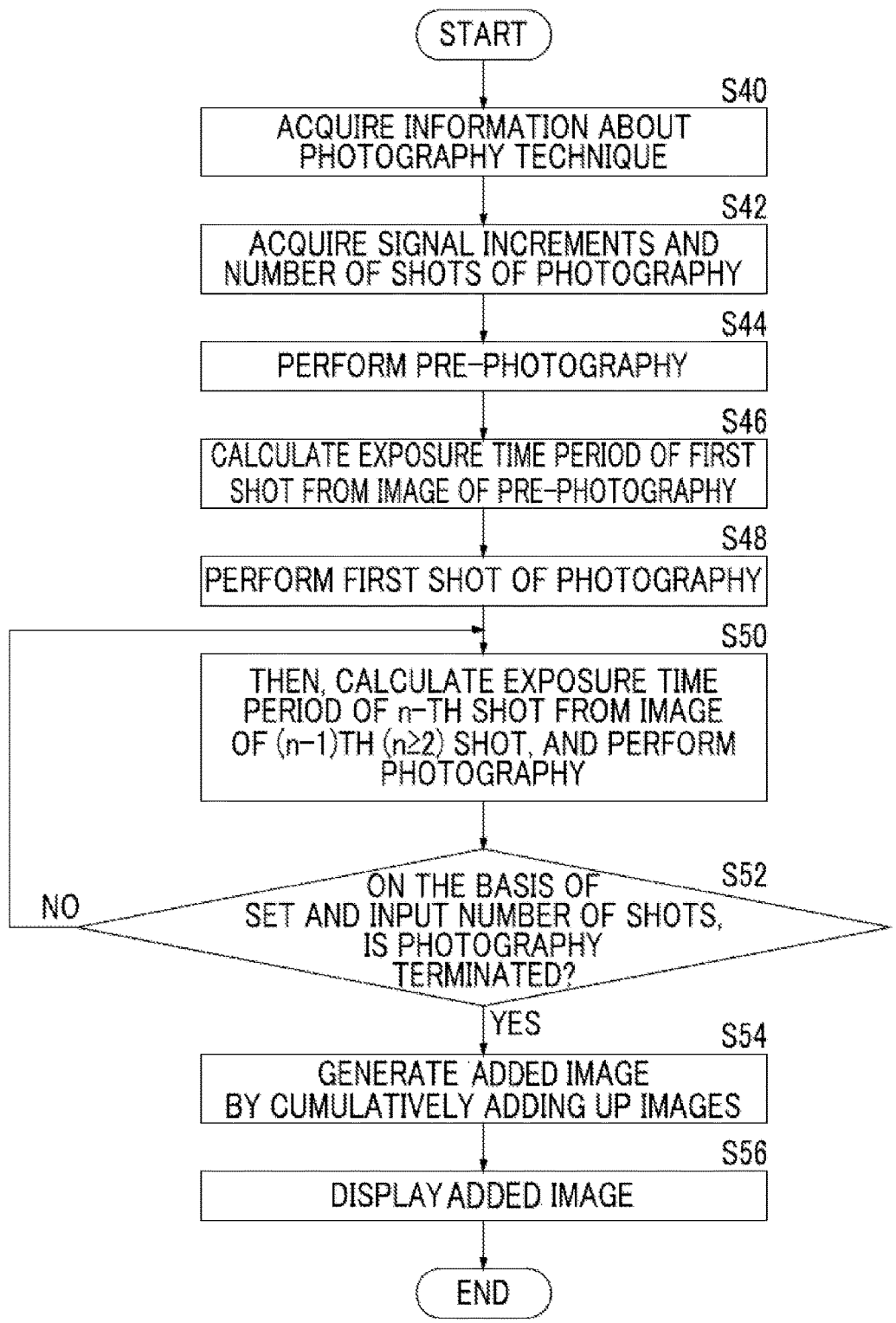
FIG. 8 is a flowchart illustrating operations of a photographing system using a photographing apparatus according to a third embodiment of the present invention.

Hereinafter, operations of the photographing system 1 of the third embodiment will be described focusing on the method of calculating each exposure time period for each shot of the photography in the above-mentioned exposure time calculation section 112. FIG. 8 is a flowchart illustrating the operations of the photographing system 1 according to another embodiment mentioned above.

First, a user sets and inputs the information about the photography technique through the input section 104, and the set and input information about the photography technique is acquired by the photographic subject light information acquisition section 110 (S40).

Next, a user sets and inputs the desired number of shots of the photography and a signal increment to be acquired in each shot of the photography through the input section 104, and the set and input number of shots of the photography and the signal increment of each shot of the photography are acquired by the exposure time calculation section 112 (S42). As the desired number of shots of the photography, the number of shots of the photography, at which it is expected that a noise amount of the added image is restricted to be within a desired range, is set and input. As the signal increment, a signal increment, which a user wants to add to the image at each shot of the photography, is set and input.

Next, after the above-mentioned setting and inputting, pre-photography is performed before actual photography (S44). It should be noted that the actual photography means photography which is performed to obtain an image for analyzing and examining a subject, and the pre-photography means photography which is performed in advance to obtain information for determining an exposure time period of the actual photography. For example, the pre-photography is performed by acquiring an exposure time period of the pre-photography according to a designated photography technique with reference to a table in which the exposure time periods of the pre-photography are associated with the photography techniques and performing photography with this exposure time period.

Specifically, the photographing section 20 is controlled on the basis of the control signal which is output from the control section 114 of the photography control device 100, and performs pre-photography (S44). The image signal acquired by the pre-photography is output to the exposure time calculation section 112.

The exposure time calculation section 112 calculates an exposure time period of a first shot of the actual photography on the basis of the image signal acquired through the pre-photography and the information about the photography technique acquired by the photographic subject light information acquisition section 110 (S46).

Specifically, the exposure time calculation section 112 reads a function corresponding to a photography technique, determines an initial value of the function on the basis of the image signal acquired by the pre-photography, and calculates each exposure time period for each shot of the photography on the basis of the determined function and the signal increments of the shots of the photography which are set and input by a user.

For example, in the case where the photography technique is the first photography technique, that is, if the light from the photographic subject is chemiluminescent, the exposure time calculation section 112 reads the above-mentioned preset attenuation function $y=y_\alpha \cdot \exp(-k \cdot t)$ of approximating the time-varying characteristics of the chemiluminescent light. Then, a signal value per the unit time period is acquired by dividing the image signal acquired by the pre-photography by the exposure time period of the pre-photography, and the signal value is set as $y_\alpha$, thereby determining the attenuation function. It should be noted that the coefficient k of the attenuation function described herein is set in advance. Further, the attenuation function is not limited to the decreasing exponential function, and may be a linear function of which a slope is negative.

Figure 9:
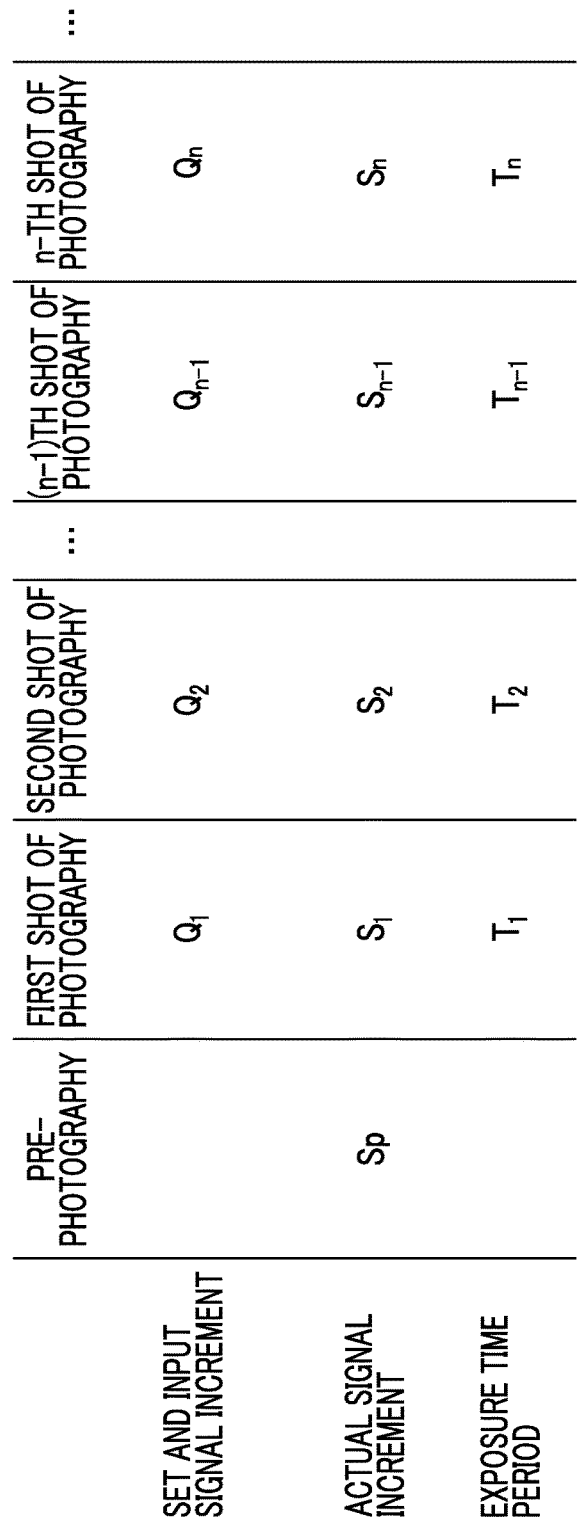
FIG. 9 is a table showing examples of exposure time periods, actual signal increments, and signal increments which are set and input by a user for shots of photography.
Figure 10:
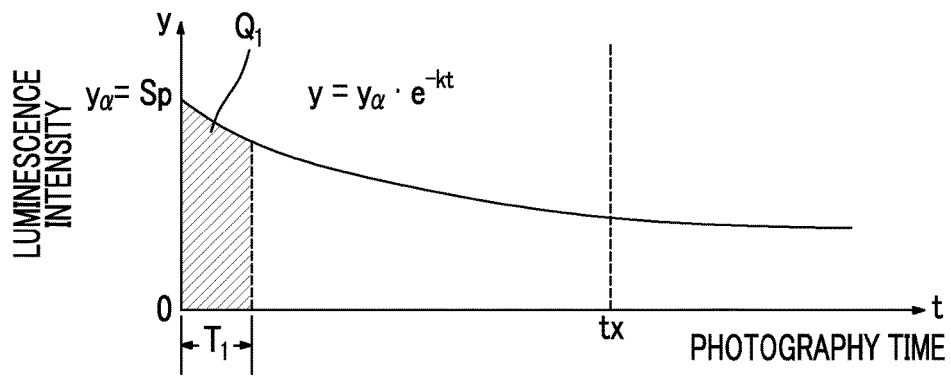
FIG. 10 is a diagram illustrating a method of calculating an exposure time period of a first shot of the photography on the basis of an image of pre-photography.

Specifically, for example, as shown in FIG. 9, assuming the signal value per the unit time period calculated through the pre-photography is $S_p$ as shown in FIG. 9, the $S_p$ is set as $y_\alpha$ as shown in FIG. 10, thereby determining the attenuation function.

Then, the exposure time calculation section 112 calculates an exposure time period, at which the signal increment of the first shot of the photography is equal to the signal increment which is set and input by a user, by using the attenuation function determined as described above. Specifically, as shown in FIG. 10, a time period $T_1$, at which a value of an integral of the attenuation function is equal to the signal increment $Q_1$ of the first shot of the photography which is set and input by a user, is calculated, and the time period $T_1$ is set as the exposure time period of the first shot of the photography. In addition, the value of the integral described herein is defined as a value which is obtained by setting a length of a predetermined photography interval in the function shown in FIG. 4A as the exposure time period and integrating the attenuation function with respect to the length of the exposure time period. Hereinafter, as necessary, a description will be given with reference to FIGS. 9 to 12.

Subsequently, the exposure time period $T_1$ calculated by the exposure time calculation section 112 is output to the control section 114, the control section 114 outputs a control signal based on the input exposure time period $T_1$ to the photographing section 20, and the photographing section 20 performs the first shot of the photography in the exposure time period $T_1$ on the basis of the input control signal (S48).

Next, the image signal acquired through the first shot of the photography is output to the exposure time calculation section 112, and the exposure time calculation section 112 acquires the signal value $S_1$ per the unit time period by dividing the image signal acquired through the first shot of the photography by the exposure time period $T_1$ of the first shot (refer to FIG. 9).

Figure 11:
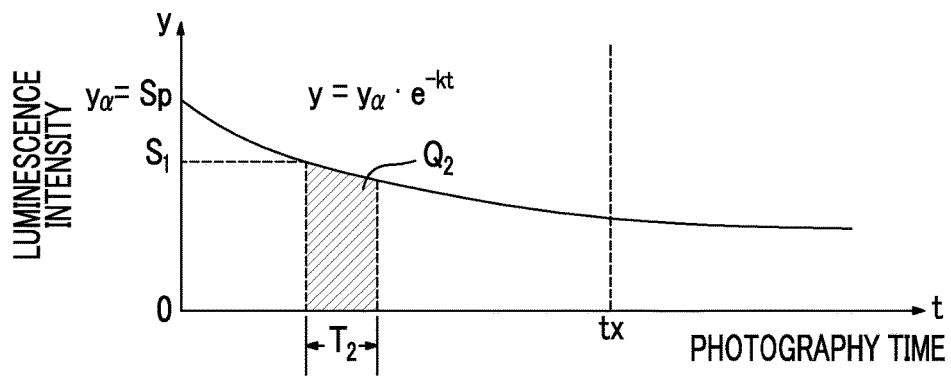
FIG. 11 is a diagram illustrating a method of calculating an exposure time period of a second shot of the photography on the basis of an image of the first shot of the photography.

Subsequently, as shown in FIG. 11, the exposure time calculation section 112 sets a signal value $S_1$ acquired through the first shot of the photography as a value of y of the attenuation function, calculates a time period $T_2$, at which a value of an integral of the function obtained from a photography time period t at this time is equal to a signal increment $Q_2$ of the second shot of the photography which is set and input by a user, and sets the time period $T_2$ as an exposure time period of the second shot of the photography.

For the second and following shots of the photography performed as described above, in a manner same as the above-mentioned manner, on the basis of the image signal of the (n−1)th (n≥2) shot of the photography, the exposure time period of the n-th shot of the photography is calculated. That is, the image signal acquired through the (n−1)th shot of the photography is output to the exposure time calculation section 112, and the exposure time calculation section 112 acquires the signal value $S_{n-1}$ per the unit time period by dividing the image signal acquired through the (n−1)th shot of the photography by the exposure time period $T_{n-1}$ of the (n−1)th shot (refer to FIG. 9).

Figure 12:
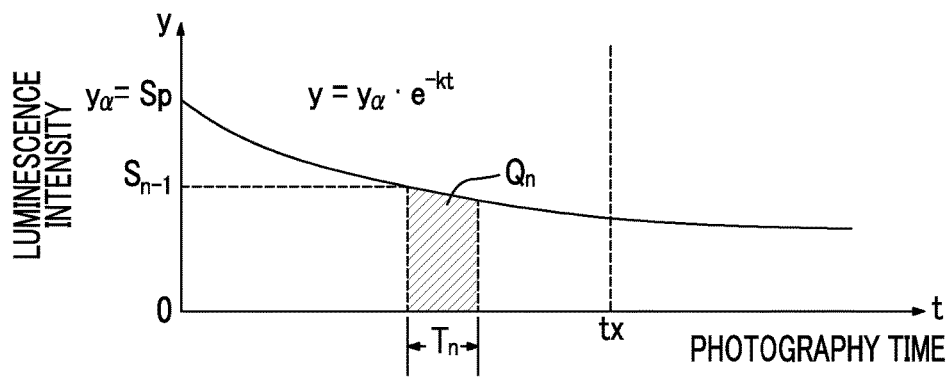
FIG. 12 is a diagram illustrating a method of calculating an exposure time period of an n-th shot of the photography on the basis of an image of an (n−1)th shot.

Subsequently, as shown in FIG. 12, the exposure time calculation section 112 sets a signal value $S_{n-1}$ acquired through the (n−1)th shot of the photography as a value of y of the attenuation function, calculates a time period $T_n$, at which a value of an integral of the function obtained from a photography time period t at this time is equal to a signal increment $Q_n$ of the n-th shot of the photography which is set and input by a user, and sets the time period $T_n$ as an exposure time period of the n-th shot of the photography.

Then, calculation of the exposure time periods for the second and following shots of the photography performed as described above and photography based on the calculated exposure time periods for the shots of the photography are performed, where the number of calculation operations and the number of photography operations are equal to the number of shots of the photography which is set and input by a user (S50 and S52).

Subsequently, the image signals, which are photographed by the photographing section 20, are sequentially output to the image processing section 108, and the image processing section 108 generates an added image signal by cumulatively adding up the image signals which are sequentially input, and outputs the added image signal to the display control section 115 (S54).

The display control section 115 generates a display control signal on the basis of the input added image signal, and outputs the display control signal to the display section 106, thereby causing the display section 106 to display the added image (S56). It should be noted that, as the added image displayed on the display section 106, only the added image, in which all the photographed images are added up, may be displayed, and the image of the first shot of the photography and added images, which are generated for shots of the photography, may be also displayed. That is, for example, in the case where photography is performed three times, the following images may be arranged and displayed: the first shot image of the photography; an added image in which the first shot image of the photography and the second shot image of the photography are added up; and an added image in which the first shot image of the photography, the second shot image of the photography, and the third shot image of the photography are added up.

The method of calculating the exposure time period for each shot of the photography in the case where the photography technique is the first photography technique has been hitherto described.

In contrast, in the case where the photography technique is the second photography technique, that is, in the case where the light from the photographic subject is fluorescent, regarding the exposure time period of the first shot of the photography, the exposure time calculation section 112 acquires the signal value $S_p$ per the unit time period by dividing the image signal acquired through the pre-photography by the exposure time period of the pre-photography, and calculates the exposure time period $T_1$ of the first shot of the photography by dividing the signal increment Q of the first shot of the photography, which is set and input by a user, by a signal value $S_p$.

Then, regarding the exposure time period for each of the second and following shots of the photography, a signal value $S_{n-1}$ per the unit time period is acquired by dividing the image signal of the (n−1)th shot (n≥2) of the photography by an exposure time period $T_{n-1}$ of the (n−1)th shot, and an exposure time period $T_n$ of the n-th shot of the photography is calculated by dividing a signal increment $Q_n$ of the n-th shot of the photography, which is set and input by a user, by a signal value $S_{n-1}$.

Subsequently, in a manner same as the above-mentioned first photography technique, the image processing section 108 generates an added image, and the display control section 115 causes the display section 106 to display the added image.

According to the photographing system 1 of the third embodiment, when a subject is photographed a plurality of times sequentially, the exposure time period of the n-th shot of the photography is calculated on the basis of the images captured through the (n−1)th shot or previous shots than the (n−1)th shot of the photography, that is, the exposure time period is calculated on the basis of the images which are acquired until the previous shot of the photography. Therefore, it is possible to automatically calculate an appropriate exposure time period in consideration of temporal change in light at a time point of the previous shot of the photography, regardless of a user's experience.

Since an image superposition effect (signal increment) can be expected, by appropriately setting the number of images superimposed, it is possible to prevent the image quality from deteriorating.

In the second and following shots of the photography, pre-photography is not necessary, and it is possible to shorten the time period in total.

The exposure time periods are calculated using the images of the actual photography. Therefore, for example, exposure conditions such as binning are commonly applied, and thus it is possible to further accurately calculate exposure time periods.

In the photographing system of the third embodiment, each exposure time period for each shot of the photography is calculated such that the signal increment of each image at each shot of the photography is equal to a value which is set and input by a user. However, the present invention is not limited to this, and each exposure time period for each shot of the photography may be calculated such that a sum value of the signal increments of each image at each shot of the photography is equal to the value which is set and input by a user.

Figure 13:
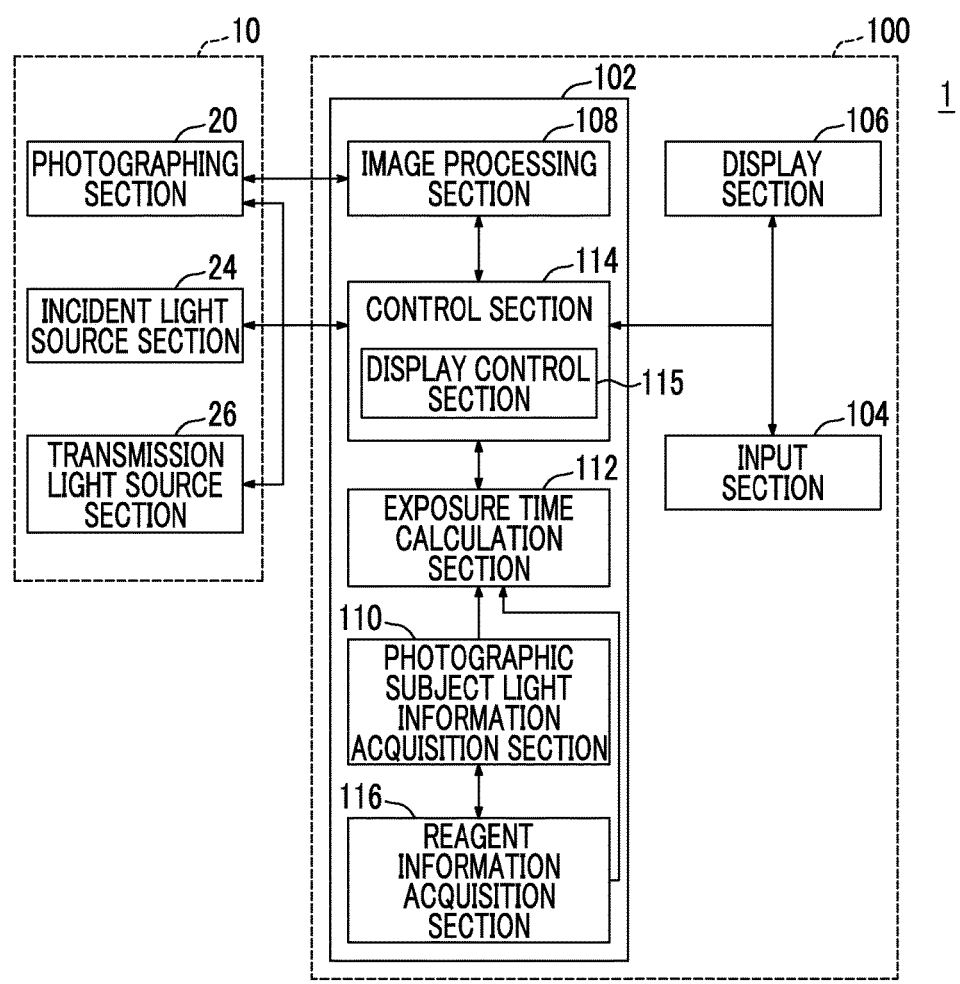
FIG. 13 is a schematic block diagram of a modification example of a photographing system using a photographing apparatus according to an embodiment of the present invention.

In the photographing system 1 of the third embodiment, as shown in FIG. 13, a reagent information acquisition section 116 may be further provided, and the exposure time calculation section 112 may select the method of calculating the exposure time period for each shot of the photography on the basis of the information of the reagent acquired by the reagent information acquisition section 116, and may calculate each exposure time period for each shot of the photography by using the selected method of calculating the exposure time period. The information about the reagent is set and input by a user through the input section 104. For example, the information is information about a substance (for example, a chemiluminescence substrate) relating to chemiluminescence in the case where chemiluminescent light is photographed, and is information about a fluorescent substance in the case where fluorescent light is photographed.

Specifically, for example, a table as the following Table 2 may be set in the exposure time calculation section 112 in advance. In the table, pieces of the information about the photography technique and the reagent are associated with functions which are used when calculating the exposure time period for each shot of the photography. The exposure time calculation section 112 may acquire a corresponding function with reference to the table on the basis of the information about the photography technique acquired by the photographic subject light information acquisition section 110 and the information about the reagent acquired by the reagent information acquisition section 116, and may calculate each exposure time period for each shot of the photography by using the function same as the above-mentioned manner. It should be noted that, as the functions which are set in the table, a numerical expression indicating the function may be set, and types of function such as exponential functions, constant functions, and linear functions and coefficients of the functions may be set in the table.

For example, the item No. 1 is a case where there is no setting about the reagent name in the first photography technique. In this case, the exposure time calculation section 112 acquires the attenuation function $F_0$, and calculates each exposure time period for each shot of the photography by using the attenuation function $F_0$. Further, for example, the item No. 5 is a case where the fluorescent substance name $B_1$ is set and input as the reagent name in the second photography technique. In this case, the exposure time calculation section 112 acquires the attenuation function $G_1$, and calculates each exposure time period for each shot of the photography by using the attenuation function $G_1$. In the above-mentioned embodiment, the method of calculating the exposure time periods in the case of approximating the time-varying characteristics of fluorescent light by the constant function was described. In the case where the characteristics are approximated by the linear function such as the attenuation function $G_1$, in a manner same as the first photography technique, exposure time periods may be calculated such that a value of an integral of the function is equal to the set and input signal increment.

TABLE 2

| No. | Photography technique (detection target) | Reagent Name | Function |
| --- | --- | --- | --- |
| 1 | First Photography Technique | — | $F_0: y = y_\alpha \cdot \exp(-kt)$ |
| 2 | (Chemiluminescent Light) | $A_1$ | $F_1: y = y_\alpha \cdot \exp(-k_1 t)$ |
| 3 | | $A_2$ | $F_2: y = y_\alpha \cdot \exp(-k_2 t)$ |
| 4 | Second Photography Technique | — | $G_0: y = -a \cdot t + y_\gamma$ |
| 5 | (Fluorescent Light) | $B_1$ | $G_1: y = -a_1 \cdot t + y_\gamma$ |
| 6 | | $B_2$ | $G_2: y = -a_2 \cdot t + y_\gamma$ |
| 7 | | $B_3$ | $G_3: y = y_\gamma$ |

It is preferable to set Table 2 such that a user may modify the items thereof and may add another item thereto. For example, it can be considered that exponential approximation may be changed to linear approximation, the slope of linear approximation may be changed, or a new item may be added. In the case where contents of Table 2 can be changed using the input section 104, for example, various kinds of the reagent can be handled. Further, in the case where the light amount of the illumination light is changed by deterioration of the light source, approximation can be performed on the time-varying characteristics of the illumination light through the attenuation function or the constant function in which the deterioration of the light source is considered.

Figure 14:
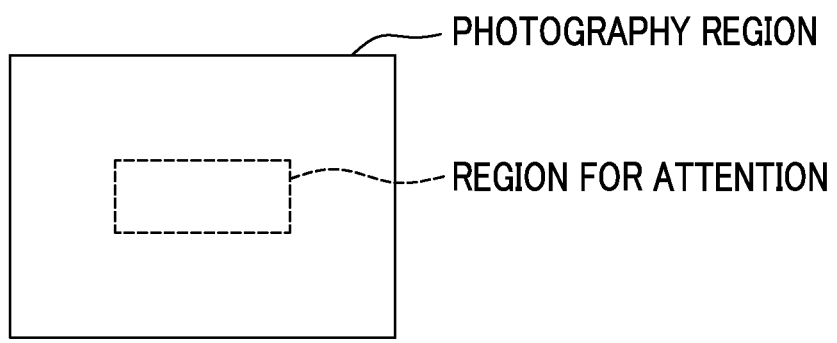
FIG. 14 is a diagram illustrating an example of a region for attention.

In the photographing system 1 of the third embodiment, as the image signals of the pre-photography and actual photography used for when the signal value per the unit time period is calculated, it is possible to use a maximum value, a representative value, an average value, or a mode value in the image. Alternatively, a maximum value, a representative value, an average value, or a mode value in a predetermined region for attention in the image acquired by the pre-photography and the actual photography may be used. For example, as shown in FIG. 14, the region for attention may be set in the center portion in a photography region (in the image). However, the present invention is not limited to this, and the region for attention may be set in a different portion. Further, for example, the region for attention may be designated by a user through the input section 104 (which corresponds to the region for attention designation receiving section) while the user views the image of the pre-photography displayed on the display section 106. In addition, an important region in a subject may be automatically detected, and the detected region may be set as the region for attention. Furthermore, instead of the region for attention, a predetermined pixel for attention may be set, and an exposure time period may be calculated using the signal value of the pixel for attention per the unit time period.

In the photographing system 1 of the third embodiment, as described above, the exposure time period for each shot of the photography is calculated on the basis of the image signal acquired by the previous shot of the photography, a function of approximating the time-varying characteristics of light, and the signal increment which is set and input by a user. However, for example, the luminescence intensity of the light may be greater than a value of the approximation function, the value of the signal increment, which is set and input by a user, may be excessively large, and thus the image signal of the previous shot of the photography may be saturated. In this case, it may be difficult to calculate an appropriate exposure time period. It should be noted that the saturation described herein is saturation of an imaging element in the photographing section 20.

Figure 15:
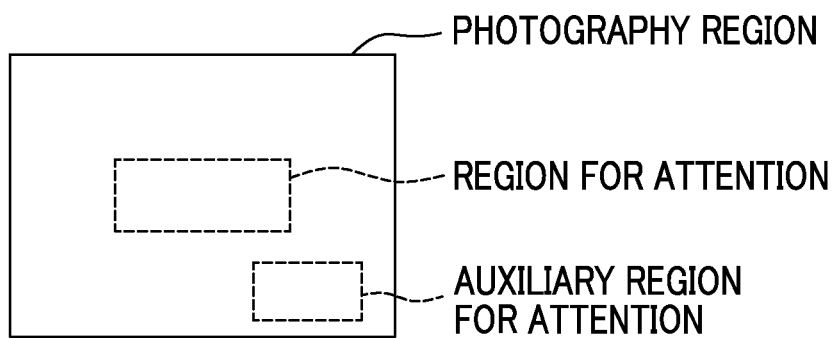
FIG. 15 is a diagram illustrating an example of a region for attention and an auxiliary region for attention.

Accordingly, in the case of calculating the exposure time period on the basis of the image signal of the above-mentioned region for attention or pixel for attention (hereinafter referred to as the region for attention or the like), the image signal of the region for attention or the like may be saturated. In this case, as shown in FIG. 15, an auxiliary region for attention or an auxiliary pixel for attention (hereinafter referred to as the auxiliary region for attention or the like) may be set at a position different from that of the region for attention or the like, and an exposure time period may be calculated on the basis of the image signal of the auxiliary region for attention or the like. For example, as shown in FIG. 14, the auxiliary region for attention or the like may be set in a peripheral portion in the photography region (image). However, the present invention is not limited to this, and the auxiliary region for attention or the like may be set at a different position. Further, in a manner same as the region for attention or the like, a user may designate the position thereof, a region or the like of which an image signal is smaller than a preset threshold value may be automatically extracted, or a region or the like of which an image signal is relatively small in the photography region may be automatically extracted, and the region may be set as the auxiliary region for attention or the like.

As described above, in the case where the exposure time period is calculated on the basis of the image signal of the auxiliary region for attention or the like, a ratio of the image signal of the auxiliary region for attention or the like to the region for attention or the like, of which the image signal is not saturated, may be calculated, and the exposure time period may be calculated on the basis of the ratio, the image signal of the auxiliary region for attention or the like, and the signal increment which is set and input by a user. Specifically, for example, in the case where an actual signal increment of the unsaturated region for attention or the like is 20000 and the actual signal increment of the auxiliary region for attention or the like is 2000, the ratio thereof is 10:1. Consequently, for example, if the signal increment which is set and input by a user is 60000 and the image signal of the region for attention or the like is saturated by the photography, the exposure time period may be calculated such that the signal increment of the auxiliary region for attention or the like is 6000.

In the case where the image signal of the above-mentioned region for attention or the like is saturated, the image processing section 108 may acquire the image signal of the desired exposure time period by adding up the images which are adjusted to the unsaturated image signal by using a time proportionality factor. Specifically, for example, in the case where the image signal of the image photographed in the exposure time period of 10 seconds is saturated, by multiplying the unsaturated image signal of the photography in the exposure time period of 1 second by 10, the image signal of the photography in the exposure time period of 10 seconds may be acquired. Thereby, it is possible to acquire a high dynamic range image.

In the photographing system of the third embodiment, the exposure time period of the first shot of the photography is calculated on the basis of the image signal of the single shot of the pre-photography. However, the present invention is not limited to this, and the exposure time period of the first shot of the photography may be calculated on the basis of the image signals of a plurality of shots of the pre-photography. Specifically, for example, the signal value per the unit time period may be acquired by adding up the image signals of the plurality of shots of the pre-photography and dividing the added image signal by a time period which is obtained by adding up the exposure time periods of the plurality of shots of the pre-photography, and the signal value may be an initial value of the function of approximating the time-varying characteristics of the light.

In the photographing system of the third embodiment, a preset value is used as the coefficient k of the attenuation function. However, pre-photography may be performed twice, and the coefficient k may be calculated, using image signals acquired by two shots of the pre-photography, on the basis of the following Expression 3. In the following Expression 3, $S_{p1}$ is a signal value per the unit time period of the first shot of the pre-photography, $S_{p2}$ is a signal value per the unit time period of the second shot of the pre-photography, and $T_g$ is a time period from a time point of the first shot of the pre-photography to a time point of the second shot of the pre-photography. By performing pre-photography twice in such a manner, for example, even if a reagent having unclear time-varying characteristics like a new reagent is photographed, it is possible to appropriately set the coefficient k.

$$k = \frac{\ln(S_{p1}) - \ln(S_{p2})}{T_g} \quad \text{Expression 3}$$

Also in the case of calculating the exposure time period of the actual photography, in the above-mentioned embodiment, the exposure time period is calculated on the basis of the image signal of the previous single shot of the photography. However, the present invention is not limited to this, and the exposure time period of the n-th shot of the photography may be calculated on the basis of the image signals of the (n−1)th shot or previous shots than the (n−1)th shot of the photography performed a plurality of times. Specifically, for example, the signal value per the unit time period may be acquired by adding up the image signals of the (n−1)th shot or previous shots than the (n−1)th shot of the actual photography performed a plurality of times and dividing the added image signal by a time period which is obtained by adding up the exposure time periods of the plurality of shots of the actual photography, and the exposure time period of the n-th shot of the photography may be calculated using the signal value as described above. Further, when the exposure time period of the n-th shot of the photography is calculated, as described above, the exposure time period of the n-th shot of the photography may be calculated using not only the image signals of the (n−1)th shot or previous shots than the (n−1)th shot of the actual photography but also the image signal of the single shot or the image signals of the plurality of shots of the pre-photography.

In the photographing system of the third embodiment, the total photography time period, which is obtained by adding up the exposure time periods of all the shots of the photography, is calculated, and the display control section 115 causes the display section 106 to display the total photography time period.

In the photographing system of the third embodiment, it is preferable that a sensitivity of the photography is increased by performing binning when pre-photography is performed. When the binning is performed as described above, the signal value $S_p$ per the unit time period of the pre-photography is converted into a signal value $S_m$ on the basis of the following Expression 4. In the following Expression 4, $B_p$ is a binning number of the pre-photography, and $B_m$ is a binning number of the actual photography.

$$S_m = S_p \frac{B_m}{B_p} \qquad \text{Expression 4}$$

What is claimed is:

1. A photographing apparatus comprising:
an image sensor that photographs a subject a plurality of times sequentially; and
a processor configured to:
acquire information about a type of light from the subject of the photography,
select one method of a plurality of methods of calculating an exposure time period of the photography that are set in advance according to time-varying characteristics of a plurality of the types of the light on the basis of the information about the type of the light acquired by the processor, and
calculate each exposure time period for each shot of the photography, by using the selected method of calculating the exposure time period,
wherein the image sensor performs the photography, on the basis of each exposure time period which is calculated by the processor for each shot of the photography,
wherein the processor is further configured to acquire information about a reagent used at the time of photographing the subject, and
wherein the processor is further configured to select a method of calculating the exposure time period of the photography on the basis of the information about the light and the information about the reagent, and calculates each exposure time period for each shot of the photography by using the selected method of calculating the exposure time period.

2. The photographing apparatus according to claim 1, wherein the processor accesses a table in which the method of calculating the exposure time period of the photography is associated with the information about the light and the information about the reagent.

\* \* \* \* \*